US011530251B2

(12) United States Patent
Rutenberg et al.

(10) Patent No.: US 11,530,251 B2
(45) Date of Patent: Dec. 20, 2022

(54) METHODS FOR CANCER THERAPY USING ISOLATED NTB-A ECTODOMAIN POLYPEPTIDES

(71) Applicant: HADASIT MEDICAL RESEARCH SERVICES AND DEVELOPMENT LTD, Jerusalem (IL)

(72) Inventors: Abraham Rutenberg, Haifa (IL); Ronny Uzana, Rehovot (IL); Michal Lotem, Reut (IL); Arthur Machlenkin, Givat Brener (IL); Galit Eisenberg, Modiin (IL); Tamar Peretz-Yablonsky, Jerusalem (IL); Shoshana Frankenburg, Jerusalem (IL); Roni Engelstein, Jerusalem (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 135 days.

(21) Appl. No.: 16/417,048

(22) Filed: May 20, 2019

(65) Prior Publication Data
US 2019/0330303 A1 Oct. 31, 2019

Related U.S. Application Data

(62) Division of application No. 15/110,111, filed as application No. PCT/IL2015/050033 on Jan. 8, 2015, now Pat. No. 10,344,073.

(60) Provisional application No. 61/925,265, filed on Jan. 9, 2014.

(51) Int. Cl.
| | | |
|---|---|---|
| *C07K 14/705* | (2006.01) | |
| *A61K 38/17* | (2006.01) | |
| *A61K 35/17* | (2015.01) | |
| *A61P 35/00* | (2006.01) | |
| *C12N 5/0783* | (2010.01) | |
| *A61K 39/39* | (2006.01) | |
| *A61K 39/395* | (2006.01) | |
| *A61K 45/06* | (2006.01) | |
| *C07K 16/28* | (2006.01) | |
| *A61K 39/00* | (2006.01) | |

(52) U.S. Cl.
CPC ........ *C07K 14/70503* (2013.01); *A61K 35/17* (2013.01); *A61K 38/1774* (2013.01); *A61K 39/39* (2013.01); *A61K 39/3955* (2013.01); *A61K 45/06* (2013.01); *C07K 16/2803* (2013.01); *C12N 5/0638* (2013.01); *A61K 2039/505* (2013.01); *A61P 35/00* (2018.01); *C07K 2317/75* (2013.01); *C12N 2501/998* (2013.01)

(58) Field of Classification Search
CPC .............. A61K 39/39; A61K 2039/505; A61K 14/70503; A61K 38/1774; A61K 35/17; A61P 35/00; C07K 2317/75
See application file for complete search history.

(56) References Cited

U.S. PATENT DOCUMENTS

| | | | |
|---|---|---|---|
| 4,376,110 A | 3/1983 | David | |
| 4,522,811 A | 6/1985 | Eppstein | |
| 4,816,567 A | 3/1989 | Cabilly | |
| 5,225,539 A | 7/1993 | Winter | |
| 5,545,807 A | 8/1996 | Surani | |
| 5,693,761 A | 12/1997 | Queen | |
| 5,693,762 A | 12/1997 | Queen | |
| 6,284,267 B1 | 9/2001 | Aneja | |
| 6,660,843 B1 | 12/2003 | Feige | |
| 6,887,470 B1 | 5/2005 | Bridon | |
| 6,926,898 B2 | 8/2005 | Rosen | |
| 7,592,313 B2* | 9/2009 | Zheng | .............. G01N 33/56972 424/134.1 |
| 2003/0191056 A1 | 10/2003 | Walker | |
| 2003/0195154 A1 | 10/2003 | Walker | |
| 2005/0054051 A1 | 3/2005 | Rosen | |
| 2006/0099177 A1 | 5/2006 | June | |
| 2009/0017014 A1 | 1/2009 | Valdez | |
| 2009/0181009 A1* | 7/2009 | Abo | ................. G01N 33/57426 424/130.1 |
| 2010/0150886 A1 | 6/2010 | Marui | |
| 2011/0160642 A1 | 6/2011 | Neuberger | |

(Continued)

FOREIGN PATENT DOCUMENTS

| | | |
|---|---|---|
| EP | 2083088 A2 | 7/2009 |
| JP | 2005-206478 A | 8/2005 |

(Continued)

OTHER PUBLICATIONS

Korver et al., The lymphoid cell surface receptor NTB-A: a novel monoclonal antibody target for leukemia and lymphoma therapeutics, Blood, 2008, 112(11):4975.*

(Continued)

*Primary Examiner* — Hong Sang
(74) *Attorney, Agent, or Firm* — Rothwell, Figg, Ernst & Manbeck, P.C.

(57) ABSTRACT

The present invention is directed to the field of immunotherapy. Specifically, the invention provides compositions and methods for improved T cell modulation ex vivo and in vivo and for the treatment of cancer and other pathologies. More specifically, embodiments of the invention are directed to the use of soluble NTB-A polypeptides or agonists thereof for the treatment of cancer patients, for preventing and treating cytopenia in susceptible patients, and for the ex vivo preparation of improved cell compositions.

7 Claims, 11 Drawing Sheets

Specification includes a Sequence Listing.

(56) References Cited

U.S. PATENT DOCUMENTS

| | | |
|---|---|---|
| 2011/0171204 A1 | 7/2011 | Abo |
| 2012/0244133 A1 | 9/2012 | Rosenberg |

FOREIGN PATENT DOCUMENTS

| | | | |
|---|---|---|---|
| WO | 86/01533 A1 | 3/1986 | |
| WO | WO 90/07861 A1 | 7/1990 | |
| WO | WO 97/02671 A2 | 1/1997 | |
| WO | 03/008449 A1 | 1/2003 | |
| WO | WO-03008449 A1 * | 1/2003 | ............ A61P 31/12 |
| WO | 2006/037421 A2 | 4/2006 | |
| WO | 2007045996 A1 | 4/2007 | |
| WO | 2020261265 A1 | 12/2020 | |
| WO | 2020261266 A1 | 12/2020 | |

OTHER PUBLICATIONS

Falco et al., Homophilic interaction of NTBA, a member of the CD2 molecular family: induction of cytotoxicity and cytokine release in human NK cellsEur. J. Immunol., 2004, 34:1663-1672.*
Valdez et al., NTB-A, a New Activating Receptor in T Cells That Regulates Autoimmune Disease, J. B. C, 2004, 279(18): 18662-18669.*
English translation of JP2005206478, pub. date: Aug. 4, 2005.*
Martin et al., BioTechniques, 2019, 66(4): 167-170.*
NCT00612664, first posted on Jan. 30, 2008.*
Choo et al., BMC Bioinformatics, 2009, 10(Suppl 15):S2, pp. 1-12.*
Rutenberg et al., The Fifth Annual Meeting of the Israeli Society for Cancer Research (ISCR), the 2013 Cancer Route-Stem Cells, the Microenvironment, Gene Regulation and Novel Therapies, May 23, 2013.*
Accession No. Q96DU3, isoform 1, retrieved on Dec. 27, 2016, from https://www.ncbi.nlm.nih.gov/protein/Q96DU3.3 , 11 Pages.
Bendig (1995) Humanization of rodent monoclonal antibodies by CDR grafting. Methods: A Companion to Methods in Enzymology, 8, 83-93.
Chatterjee et al., (2011) SLAMF6-driven co-stimulation of human peripheral T cells is defective in SLE T cells. Autoimmunity, 44(3), 211-8; pp. 1-14.
Dolman (1994) Effects of amino acid sequence changes on antibody-antigen interactions. Res Immunol, 145(1), 33-36.
Crawford et al., (2004) Chemotherapy-induced neutropenia: risks, consequences, and new directions for its nanagement. Cancer, 100(2), 228-237.
Eisenberg et al., (2014), Discovery of the immune modulatory role of SLAMF6 trough tumor-CD8-cell interactions p. 80 [online], [retrieved on Apr. 2, 2015], Retrieved from the Internet http://www.iscr.org.il/image/users/124131/ftp/my_files/pdf/%D7%A4%D7%95%D7%A1%D7%98%D7%A8%D7%99%D7%9D%20%D7%95%D7%AA%D7%A7% D7%A6%D7%99%D7%A8%D7%99%D7%9D%20%D7%9C%D7%90%D7%AA%D7%A8%20%D7%9E%D7%A2%D7%95%D7%93%D7%9B%D7%9F.pdf?id=16323521.
Eisenberg et al., (2018) Soluble SLAMF6 receptor induces strong CD8+ T cell effector function and improves anti-melanoma activity in vivo. Cancer Immunol Res; 33 pages.
Elflein et al., (2003) Rapid recovery from T lymphopenia by CD28 superagonist therapy. Blood, 102(5), 1764-1770.
Khantasup et al., (2015) Design and Generation of Humanized Single-chain Fv Derived from Mouse Hybridoma for Potential Targeting Application. Monoclon Antib Immunodiagn Immunother, 34(6), 404-417.
Korver et al., (2007) The lymphoid cell surface receptor NTB-A: a novel monoclonal antibody target for leukaemia and lymphoma therapeutics. British journal of haematology, 137(4), 307-318.

Fv Structure and Diversity in Three Dimensions. In: Fundamental Immunology, edited by Paul WE. Raven Press, New York, USA. 1993; pp. 292-295.
Rudikoff et al., (1982) Single amino acid substitution altering antigen-binding specificity. Proc Natl Acad Sci U S A, 79(6), 1979-1983.
Snow et al., (2009) Restimulation-induced apoptosis of T cells is impaired in patients with X-linked lymphoproliferative disease caused by SAP deficiency. The Journal of clinical investigation, 119(10), 2976-2989.
Snow et al., (2010) The power and the promise of restimulation-induced cell death in human immune diseases. Immunological reviews, 236(1), 68-82.
Uzana et al., (2012) Trogocytosis is a gateway to characterize functional diversity in melanoma-specific CD8+ T cell clones. The Journal of Immunology, 188(2), 632-640.
Valdez et al., (2004) NTB-A, a new activating receptor in T cells that regulates autoimmune disease. Journal of Biological Chemistry, 279(18), 18662-18669.
Wu et al., (2012) Adoptive T-Cell Therapy Using Autologous Tumor-Infiltrating Lymphocytes for Metastatic Melanoma Current Status and Future Outlook. The Cancer Journal, 18(2), 160-175.
Dutta and Schwartzberg (2012) Characterization of Ly108 in the thymus: evidence for distinct properties of a novel form of Ly108. J Immunol 188(7): 3031-3041.
Ji et al., (2014) Identification of the genomic insertion site of Pmel-1 TCR α and β transgenes by next-generation sequencing. PLoS One 9(5): e96650; 8 pages.
Overwijk et al., (2003) Tumor regression and autoimmunity after reversal of a functionally tolerant state of self-reactive CD8+ T cells. J Exp Med 198(4): 569-580.
Bottino et al., (2001) NTB-A [correction of GNTB-A], a novel SH2D1A-associated surface molecule contributing to the inability of natural killer cells to kill Epstein-Barr virus-infected B cells in X-linked lymphoproliferative disease. J Exp Vied 194(3): 235-246.
Eisenberg et al., (2018) Soluble SLAMF6 Receptor Induces Strong CD8+ T-cell Effector Function and Improves Anti-Melanoma Activity In Vivo. Cancer Immunol Res 6(2): 127-138.
Hajaj et al., (2020) Alternative splicing of SLAMF6 in human T cells creates a co-stimulatory isoform that counteracts the inhibitory effect of the full-length receptor. bioRxiv 2020.08.21.262238; doi: https://doi.org/10.1101/2020.08.21.262238.
Hajaj et al., (2020) SLAMF6 deficiency augments tumor killing and skews toward an effector phenotype revealing it as a novel T cell checkpoint. Elife 9: e52539.
Kageyama et al., (2012) The receptor Ly108 functions as a SAP adaptor-dependent on-off switch for T cell help to B cells and NKT cell development. Immunity 36(6): 986-1002.
Yigit et al., (2019) SLAMF6 as a Regulator of Exhausted CD8+ T Cells in Cancer. Cancer Immunol Res 7(9) 1485-1496.
NCBI Reference Sequence: NM_011184715.1; Homo sapiens SLAM family member 6 (SLAMF6), transcript variant 3, mRNA. Retrieved from: https://www.ncbi.nlm.nih.gov/nuccore/NM_011184715.1 on Jul. 13, 2022. 4 pages.
NCBI Reference Sequence: NM_011184716.1; Homo sapiens SLAM family member 6 (SLAMF6), transcript variant 4, mRNA Retrieved from: https://www.ncbi.nlm.nih.gov/nuccore/NM_011184716.1 on Jul. 15, 2022. 4 pages.
UniProt database entry Q96DU3; SLAF6_HUMAN. SLAM family member 6, Homo sapiens (Human), Gene: SLAMF6 (KALI). Retrieved from: https://www.uniprot.org/uniprotkb/Q96DU3/entry on Jul. 9, 2022. 10 pages.
Communication of a notice of opposition dated Jul. 25, 2022 issued in European Patent Application No. 15734922.6. 61 pages.

* cited by examiner

METHODS FOR CANCER THERAPY USING ISOLATED NTB-A ECTODOMAIN POLYPEPTIDES

FIELD OF THE INVENTION

The present invention is directed to the field of immunotherapy. Specifically, the invention provides compositions and methods providing improved T cell modulation ex vivo and in vivo, useful in the treatment of cancer and other pathologies.

BACKGROUND OF THE INVENTION

NK-T-B antigen (NTB-A), also known as signaling lymphocyte activation molecule family member 6 (SLAMF6), CD352, Ly-108, SF2000 and KALI, is a type I transmembrane protein belonging to the SLAM family of immune cell receptors. SLAM family proteins are members of the CD2 subgroup of the Ig superfamily. NTB-A is expressed on natural killer (NK), T and B cells and exhibits homotypic interactions, mediated by recruitment of SLAM associated protein (SAP) and additional adapter proteins to the receptor complex.

NTB-A contains two extracellular immunoglobulin (Ig)-like domains and three cytoplasmic tyrosine-based signaling motifs, one of which is included in a classical immunoreceptor tyrosine-based inhibitory motif. Engagement of NTB-A on human T cells can substitute the CD28 co-stimulatory pathway and induces polarization toward a Th1 phenotype. However, CD4-positive T cells from NTB-A (Ly-108) knockout mice show impairment in IL-4 production, suggesting a role of NTB-A in Th2 polarization. The reason for this discrepancy is not fully elucidated. Activation of NTB-A on human NK cells stimulates cytotoxicity and proliferation, as well as IFN-γ and TNF-α production.

Valdez et al, 2004 teach that NTB-A activates T cells by homotypic interactions, and specifically enhances Th1 properties. An NTB-A-Fc fusion protein, produced by fusing the first 226 amino acids of NTB-A to the Fc portion of murine IgG1, was found to inhibit B cell isotype switching, commonly induced by Th1-type cytokines, and inhibited a Th1-dependent autoimmune disease (EAE model). Thus, the reported NTB-A fusion protein was found to act as an NTB-A antagonist in the experimental systems reported by Valdez et al.

US 2009/017014 to Valdez et al is directed to the PRO20080 polypeptide (having an amino acid sequence corresponding to that of NTB-A), the extracellular portion thereof, homologs, agonists and antagonists thereof, which are suggested as putative modulators of immune diseases. The '014 publication suggests the use of certain immunostimulating compounds disclosed therein in immunoadjuvant therapy for the treatment of cancer.

Uzana et al., 2012 disclose that NTB-A blockade on antigen presenting cells (APC) by specific antibodies inhibited cytokine secretion from CD8+ lymphocytes. While the publication suggests this molecule as a potential target for improving anti-cancer immunotherapy, experimental exploration of the relevance of this approach is said to be warranted, since similar approaches, targeting other co-stimulatory receptors such as CD28 with agonistic antibodies, ended up in a fatal outcome in clinical trials.

Since NTB-A is expressed on certain hematopoietic tumors, vaccination using peptide epitopes derived from this molecule has been proposed, to induce an anti-tumor immune response against tumors aberrantly expressing this antigen. For example, PCT Pub. No. WO 2006/037421 discloses 338 peptide sequences derived from HLA class II molecules of human tumor cell lines, which can be used in vaccine compositions for eliciting anti-tumor immune responses. Among these sequences is a 16 amino acid peptide corresponding to positions 103-118 of SLAMF6. In addition, targeting these epitopes with antibodies or immunotoxin conjugates thereof has been suggested. For instance, US2011171204 discloses anti-NTB-A antibodies and antigen-binding fragments thereof, and methods of using the same to bind NTB-A and treat diseases, such as hematologic malignancies, which are characterized by expression of NTB-A. Additional antibodies against NTB-A are described, for example, by Krover et al., 2007. These antibodies exerted cytotoxic effects on NTB-A expressing lymphocytes, and had no effect on T cell proliferation or cytokine secretion.

EP2083088 discloses a method for treating cancer in a patient comprising modulating the level of an expression product of a gene selected from the group consisting of inter alia SLAMF6, wherein the cancer is selected from the group consisting of melanoma, breast cancer, colon cancer, kidney cancer, liver cancer, lung cancer, ovary cancer, pancreatic cancer, prostate cancer, uterine cancer, cervical cancer, bladder cancer, stomach cancer or skin cancer. The publication discloses that the method is useful for treating a patient characterized by over-expression of said gene.

WO 03/008449 relates to NTB-A polypeptides, nucleic acid molecules encoding the same and uses thereof. The publication also relates to methods of regulating NK cells activity by regulating the activity of NTB-A in vitro, ex vivo or in vivo, and to methods of screening active compounds using NTB-A or fragments thereof, or nucleic acid encoding the same, or recombinant host cells expressing said polypeptide. Further disclosed is the use of a compound that regulates the activity of a NTB-A polypeptide in the preparation of a medicament to regulate an immune function in a subject.

X-linked lymphoproliferative disease (XLP) is a rare congenital immunodeficiency that leads to an extreme, usually fatal increase in the number of lymphocytes upon infection with Epstein-Barr virus (EBV). XLP commonly results from deficiency of SLAM-associated protein (SAP), also designated XLP1, caused by mutations in the SH2D1A gene on chromosome Xq24-25. Accordingly, NTB-A has been implicated in this pathology, as contributing to the inability of NK-cells to kill EBV-infected B-cells.

Snow et al. (2009, 2010) examined the role of NTB-A and its downstream effector SAP, in the regulation of restimulation-induced cell death (RICD) of T cells obtained from healthy donors and XLP patients. The publications report that in normal donor T cells, NTB-A is positively involved in, and necessary for, TCR-induced apoptosis. In contrast, in XLP patients this phenomenon is reversed, as NTB-A was found to contribute to RICD resistance in XLP T cells.

Interleukin-2 is a critical growth factor for lymphocytes in culture. In its absence, activated T cells cannot be maintained and are subjected to activation induced cell death. Thus, IL-2 is widely used in cell culture, for both experimental purposes and clinical applications, in the preparation of various cell compositions, vaccines and immunotherapies for cancer, autoimmune diseases, and other immune mediated pathologies.

IL-2 is also used as a therapeutic agent in vivo. For example, IL-2 is licensed by the Food and Drug Administration (FDA) for the treatment of kidney cancer, and its significant therapeutic effects on patients have been reported in many clinical trials. In clinical trials with patients with melanoma, IL-2 increased the survival rates of many individuals, which were higher than the average survival rates usually obtained with chemotherapy drugs.

However, it has been repeatedly shown that the use of IL-2 enhances the appearance of regulatory T cells, which may eventually exert an inhibitory effect. This issue is of particular relevance when using T cells in the clinical context, both in vivo for the systemic treatment of patients, and ex vivo, for the production of lymphocytes for adoptive cell therapy. A satisfactory substitution for IL-2 has not been found yet.

In addition, a major difficulty in using exogenous IL-2 and other exogenous cytokines in vivo is their high toxicity. Side effects are of considerable magnitude, particularly cardiac symptoms and dysfunctions, septic shock and fever. This requires intensive care for adverse effects remediation or control, and may also lead to discontinuation of treatment.

There remains an unmet medical need for improved therapeutic modalities for the management of cancer. In addition, further means for enhancing the propagation and activation of T cells in culture and for providing improved cell vaccine compositions are required. Safer, more effective therapies, circumventing the drawbacks of currently used treatment, would thus be desired.

SUMMARY OF THE INVENTION

The present invention is directed to the field of immunotherapy. Specifically, the invention provides compositions and methods for improved T cell modulation ex vivo and in vivo and for the treatment of cancer and other pathologies. More specifically, embodiments of the invention are directed to the use of soluble NTB-A polypeptides or agonists thereof for the treatment of cancer patients, and for preventing and treating cytopenia in susceptible patients. Advantageous combination therapies are further provided herein, having enhanced anti-tumor effects. According to additional embodiments of the invention, NTB-A polypeptides or agonists are used in ex vivo cell culture, providing improved T cell compositions.

The invention is based, in part, on the surprising discovery that an exogenously added polypeptide corresponding to the extracellular domain of human NTB-A (NTB-A ectodomain) is capable of protecting T cells from apoptotic cell death. Unexpectedly, the NTB-A ectodomain rescued $CD8^+$ T cells from cell death and restored their vitality following ionizing radiation and IL-2 deprivation. The invention is further based, in part, on the unexpected discovery that when co-cultured with cognate melanoma cells, T cell clones activated by the NTB-A ectodomain showed improved cytotoxicity, and elevated interferon-gamma (IFN-γ) production and surface CD137 (4-1BB) expression. In accordance, CD137, a strong co-stimulatory receptor, and NTB-A acted in synergy to triple T cell activation by melanoma cells. In addition, it is surprisingly demonstrated that when supplemented to T cell cultures, the NTB-A ectodomain gave preference to the growth and expansion of anti-tumor lymphocytes with superior activity and survivability than those achieved using IL-2, the classical T cell growth factor. The invention further demonstrates unexpectedly effective in vivo inhibition of tumor development, in a mouse model of human melanoma engraftment.

Thus, according to a first aspect of the invention, there is provided an improved method for preparing a cell composition, comprising the step of incubating ex vivo a T cell containing cell population with an effective amount of an isolated NTB-A ectodomain or an agonist thereof. According to certain embodiments, the method further comprises providing the cell population with a T cell receptor (TCR) stimulation.

According to certain advantageous embodiments, the cell compositions prepared as described herein may be used for immunotherapy. Thus, in another aspect, there is provided a method for treating cancer in a subject in need thereof, comprising:

i) obtaining a T cell containing population from the subject, or from a donor substantially histocompatible with the subject, ii) incubating the T cell containing cell population ex vivo with an effective amount of an isolated NTB-A ectodomain or an agonist thereof, and iii) administering the resulting T cell containing cell population to said subject, thereby treating cancer in said subject.

In one embodiment, the polypeptides used in the methods of the invention comprise a human NTB-A ectodomain. In another embodiment, the polypeptide consists essentially of human NTB-A ectodomain. In another embodiment, the polypeptide consists of human NTB-A ectodomain. In another embodiment, said polypeptide further comprises an epitope tag (e.g. polyhistidine tag) and/or a serum half-life elongating substance (e.g. PEG or immunoglobulin (Ig) fusion partners). Each possibility represents a separate embodiment of the invention.

In another embodiment, the use of NTB-A agonists is contemplated in the methods of the invention. An agonist as referred to herein is an agent (e.g. antibody, polypeptide or small molecule) that specifically binds to the target receptor (e.g. NTB-A) on a target cell, wherein the binding exerts a biological effect that substantially mimics the biological effects exerted via the binding of the receptor with its cognate ligand (e.g. homotypic NTB-A interactions). Thus, in another embodiment, the agonist may be an antibody specific to an NTB-A ectodomain, e.g. human NTB-A ectodomain.

The ability to expand antigen- (e.g. tumor-) specific T cells without damaging their functional capabilities is critical for successful adoptive transfer immunotherapy of patients with opportunistic infection or cancer. Antigen-specific T cells suitable for transfer can only be retrieved from blood or tissue sites in relatively small numbers. Consequently they usually are expanded specifically or nonspecifically prior to transfer. Such ex vivo manipulations, however, potentially can damage T cell homing, proliferation, and survival after infusion.

While $CD4^+$ cells respond very well to anti-CD3/CD28 stimulation, $CD8^+$ cells proliferate less extensively with an increased rate of apoptosis. One commonly used alternative approach for stimulating proliferation is the incubation of T cells with soluble anti-CD3 antibody in the presence of Fc receptor-bearing accessory cells (feeder cells), an approach designated the "Rapid Expansion Protocol" (REP). Antibody "presented" to T cells in this manner generates a more effective proliferative signal than soluble anti-CD3 alone or anti-CD3 immobilized on a plastic surface. In the treatment of cancer, adoptive cell therapy typically involves collecting T cells that are found within the tumor of the patient (referred to as tumor-infiltrating lymphocytes, TIL), which are encouraged to multiply ex vivo using high concentrations of IL-2, anti-CD3 and allo-reactive feeder cells. These T cells are then transferred back into the patient along with exogenous administration of IL-2 to further boost their anti-cancer activity. However, generation of an autologous TIL adoptive cell therapy product for re-infusion to the patient is technically challenging, and produces undesired variability, due to the use of IL-2 and feeder cells. The present invention provides in other embodiments improved methods for producing such TIL compositions for adoptive cell therapy.

In another embodiment, the population comprises CD8+ (cytotoxic) T cells (CTL). In another embodiment, the T cells are CD8+ T cells. In another embodiment, the cells are genetically engineered or modified (e.g. to exert a desired antigen specificity or any other desired trait in the eradication of malignant cells). In another embodiment, incubation with the NTB-A ectodomain polypeptide or agonist is performed in an amount and under conditions sufficient to induce or up-regulate activation markers and/or cytokines associated with T cell activation (e.g. Tc1 activation markers such as IFN-γ). Advantageously, the incubation with the NTB-A ectodomain polypeptide or agonist is performed so as to up-regulate CD137 expression on T cells. In another embodiment, the incubation is performed in the presence of T cell receptor (TCR) stimulation. In other embodiments, TCR stimulation may be antigen non-specific (performed, for example, using antibodies specific to CD3 that activate the receptor upon binding, e.g. OKT3) or antigen-specific (using suitable antigen presenting cells and antigen). In another embodiment, incubation is performed in the presence of feeder cells (e.g. allogeneic normal donor peripheral blood mononuclear cells, PBMC). According to certain advantageous embodiments, TIL compositions for adoptive cell therapy are prepared with irradiated PBMC (incapable of proliferation). In another embodiment, the incubation is performed without the addition of exogenous IL-2. In another embodiment, the incubation is performed with the addition of exogenous IL-2 ranging from 300-6000 IU/ml. In another embodiment, incubation is performed in the presence of exogenous CD137 ligand or an agonist thereof. In another embodiment, the incubation is performed in the presence of TCR stimulation and feeder cells, and without the addition of exogenous IL-2.

In another aspect, there is provided a cell composition prepared by the methods of the invention. In another embodiment, the cell composition is suitable for adoptive transfer into a recipient subject in need thereof. Thus, the composition may comprise a T cell-containing population in an amount effective for adoptive transfer immunotherapy, e.g. $10^6$ to $10^{12}$ cells.

In another aspect, there is provided a method of treating cancer in a subject in need thereof, comprising administering to the subject a cell composition of the invention, thereby treating cancer in said subject. According to certain preferable embodiments of the methods of the invention, the cell composition is histocompatible with the subject (e.g. autologous cells or MHC II-matched allogeneic cells).

In another embodiment, the method further comprises administering to the subject a therapeutically effective amount of an NTB-A ectodomain or an agonist thereof. Without wishing to be bound by a particular theory or mechanism of action, the in vivo survival of the cells following adoptive transfer to the recipient subject may be enhanced in some embodiments by administration in conjunction (concurrent or sequential) with supplementary NTB-A ectodomain or agonist thereof.

In another aspect, there is provided a method of treating cancer in a subject in need thereof, comprising administering to the subject a therapeutically effective amount of an isolated NTB-A ectodomain or an agonist thereof, thereby treating cancer in said subject.

In another embodiment, the subject to be treated by the methods of the invention is afflicted with a tumor characterized by lack of substantial NTB-A surface expression. In another embodiment, the tumor is a solid tumor. In another embodiment, the subject is afflicted with a tumor characterized by surface expression of CD137. In another embodiment, said subject is afflicted with a tumor characterized by lack of substantial NTB-A surface expression or a tumor characterized by surface expression of CD137. In another embodiment, said subject is afflicted with a tumor selected from the group consisting of: a tumor characterized by lack of substantial NTB-A surface expression, a solid tumor and a tumor characterized by surface expression of CD137. In another embodiment, the cancer is selected from the group consisting of melanoma, urinary tract cancer, gynecological cancer, head and neck carcinoma, primary brain tumor, bladder cancer, liver cancer, lung cancer, breast cancer, ovarian cancer, prostate cancer, cervical cancer, colon cancer and other cancers of the intestinal tract, bone malignancies, connective and soft tissue tumors, and skin cancers. In a particular embodiment, the cancer is melanoma.

In another embodiment, the subject is a cytopenic subject, or a subject at risk of developing cytopenia (due to e.g. irradiation or chemotherapy). In another embodiment, the subject is afflicted with or at risk of developing lymphocytopenia. In another embodiment the subject is not afflicted with X-linked lymphoproliferative disease (XLP).

The polypeptides of the invention have been demonstrated to be unexpectedly superior to IL-2, in producing safer and more effective T cell activation. Thus, the use of IL-2 may be substantially reduced and even completely replaced by the polypeptides of the invention. Accordingly, in another embodiment, the methods of the invention are affected without the addition of exogenous IL-2 (in vivo and/or ex vivo). Thus, in another embodiment, IL-2 is not exogenously administered to said subject. In another embodiment, the use of IL-2 may be reduced by at least 50%, at least 60%, at least 70%, at least 80% and preferably at least 90%.

In another embodiment, administration or addition of the NTB-A polypeptides or agonists of the invention may advantageously be performed in combination (concurrent or sequential) with administration of a CD137 ligand polypeptide or an agonist thereof (such as an anti-CD137 antibody). Non-limitative examples of such anti-CD137 antibodies which are commercially available or under clinical investigation include e.g. Bristol Myers Squibb (BMS; Princeton, N.J.) Catalog Number 663513, fully humanized IgG4 monoclonal antibody which may be used e.g. at 10-20 ng/ml, and R&D Systems Catalog Number AF838 polyclonal goat anti-4-1BB which may be used e.g. at 20-40 ng/ml.

In another embodiment, administration or addition of the NTB-A polypeptides or agonists of the invention may be performed in combination (concurrent or sequential) with administration of other signaling receptor-targeting reagents exhibiting a modifying effect on immune cell function. Examples for such reagents include e.g. antagonists or inhibitors (such as antibodies) to CTLA-4, PD-1 or PD-L1.

The polypeptides of the invention were unexpectedly demonstrated to rescue T cells from stress-induced cell death, and promote survival following irradiation or IL-2 deprivation. This is particularly surprising in view of the teachings of Snow et al., suggesting a pro-apoptotic role for NTB-A in in vitro models of restimulation-induced apoptosis.

Accordingly, in another aspect, the invention is directed to a method of reducing or inhibiting T cell death, comprising contacting T cells with an effective amount of an isolated NTB-A ectodomain or an agonist thereof.

In another embodiment, the contacting is performed in vitro (e.g. ex vivo). In another embodiment, the contacting is performed in vivo. In another embodiment, the method may be used for reducing or inhibiting T cell death in a subject suffering from or at risk of developing cytopenia.

In another aspect, there is provided a method of treating or preventing cytopenia in a subject in need thereof, comprising administering to the subject a therapeutically effective amount of an isolated NTB-A ectodomain or an agonist thereof, thereby treating or preventing cytopenia in said subject.

In some embodiments, cytopenia is associated with radiation or chemotherapy. For example, cytopenia may be cytopenia associated with high dose chemotherapy, cytopenia associated with conventional oncology therapy, drug-induced cytopenia, toxin-induced cytopenia and radiation-induced cytopenia. According to other embodiments, cytopenia may be associated with an acquired or congenital immune deficiency that is not associated with impairment in the NTB-A pathway. Thus, XLP patients are explicitly excluded from these embodiments. For example, the cytopenia may be steroid-induced, induced or exacerbated by an infectious disease (hepatitis, viral disease), or autoimmune-induced (e.g. by systemic lupus erythematosus). In a particular embodiment, the method is used for the treatment or prevention of lymphocytopenia.

In another aspect, there is provided a pharmaceutical composition comprising a therapeutic combination of 1) an isolated NTB-A ectodomain or an agonist thereof, 2) a polypeptide comprising a CD137 ligand or an agonist thereof and optionally 3) a pharmaceutically acceptable carrier.

In another embodiment the combination comprises human NTB-A ectodomain. In another embodiment the combination comprises human CD137 ligand. In another embodiment the agonist is an antibody (e.g. NTB-A specific or CD137 specific).

According to other aspects, the invention is directed to a kit containing a polypeptide comprising an NTB-A ectodomain or an agonist thereof, and instructions to use the polypeptide in the methods of the invention.

Other objects, features and advantages of the present invention will become clear from the following description and drawings.

BRIEF DESCRIPTION OF THE DRAWINGS

FIG. 3(A-D). SLAMF6 engagement by the soluble ectodomain (seSLAMF6) improves function of activated human and mouse anti-melanoma T cells.

DETAILED DESCRIPTION OF THE INVENTION

Figure 1A:
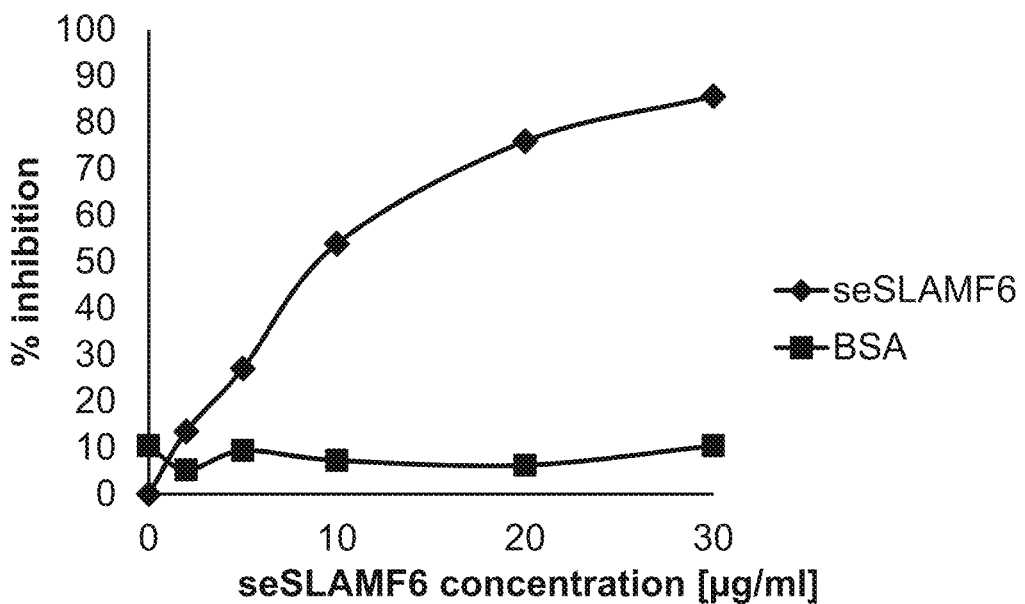
FIG. 1(A-B). seSLAMF6 (soluble ectodomain of SLAMF6) binds to SLAMF6 on tumor infiltrating lymphocytes. seSLAMF6 completely inhibits binding of anti-SLAMF6 antibodies to tumor infiltrating lymphocytes (FIG. 1A), and does not inhibit binding of anti-CD8 and anti-2B4 antibodies to these surface receptors (FIG. 1B).

The present invention is directed to the field of immunotherapy. Specifically, the invention provides compositions and methods for improved T cell modulation ex vivo and in vivo and for the treatment of cancer and other pathologies. More specifically, embodiments of the invention are directed to the use of soluble NTB-A polypeptides or agonists thereof for the treatment of cancer patients, and for preventing and treating cytopenia in susceptible patients.

Advantageous combination therapies are further provided herein, having enhanced anti-tumor effects. According to additional embodiments of the invention, NTB-A polypeptides or agonists are used in ex vivo cell culture, providing improved lymphocyte preparations.

In some embodiments, the compositions and methods of the invention employ a step comprising incubating ex vivo a T cell containing cell population with a therapeutically effective amount of an isolated (e.g. recombinantly produced) NTB-A ectodomain or an agonist thereof. In other embodiments, the methods of the invention employ a step comprising administering to a subject in need thereof a therapeutically effective amount of an isolated (e.g. recombinantly produced) NTB-A ectodomain or an agonist thereof.

In other embodiments, the invention relates to a method for treating cancer in a subject in need thereof, comprising:
  i) obtaining a T cell containing population from the subject, or from a donor substantially histocompatible with said subject,
  ii) incubating the T cell containing cell population ex vivo with an effective amount of an isolated NTB-A ectodomain or an agonist thereof, and
  iii) administering the resulting T cell containing cell population to said subject, thereby treating cancer in said subject.

According to other embodiment, the invention relates to a method of treating cancer in a subject in need thereof, comprising administering to the subject a therapeutically effective amount of an isolated NTB-A ectodomain or an agonist thereof, wherein said subject is afflicted with a tumor selected from the group consisting of: a tumor characterized by lack of substantial NTB-A surface expression, a solid tumor and a tumor characterized by surface expression of CD137.

According to additional embodiments, the invention relates to a method of reducing or inhibiting T cell death, comprising contacting T cells with an effective amount of an isolated NTB-A ectodomain or an agonist thereof.

According to further embodiments, the invention relates to a method of treating or preventing cytopenia in a subject in need thereof, comprising administering to the subject a therapeutically effective amount of an isolated NTB-A ectodomain or an agonist thereof, thereby treating or preventing cytopenia in said subject.

According to yet further embodiments, the invention relates to a method for preparing a cell composition, comprising incubating a T cell containing cell population ex vivo with an effective amount of an isolated NTB-A ectodomain or an agonist thereof, and further comprising providing the cell population with a T cell receptor (TCR) stimulation.

In yet further embodiments, the invention relates to a pharmaceutical composition comprising a therapeutic combination of 1) an isolated NTB-A ectodomain or an agonist thereof, 2) a polypeptide comprising CD137 ligand or an agonist thereof and optionally 3) a pharmaceutically acceptable carrier.

Certain particular embodiments of these methods and compositions are detailed herein below.

NTB-A Ectodomain and Agonists Thereof

The term "NTB-A" (or "SLAMF6") refers to a polypeptide having the following structural and functional properties: 1) an amino acid sequence corresponding to an art recognized (e.g. naturally occurring) mammalian NTB-A polypeptide (full length or mature form); 2) ability to specifically bind with a cell surface expressed endogenous NTB-A molecule (homotypic binding); and 3) ability to exert an agonistic NTB-A activity as described herein.

Generally, NTB-A is comprised of the following domains in the order of N' to C':

I. an N-terminal signal peptide;
II. an extracellular portion (ectodomain), comprising two conserved immunoglobulin (Ig)-like motifs: an N' Ig-like V-type domain (IgV, having a two-layered β-sheet structure, with predominantly neutral, albeit polar, front surfaces), and a C' Ig-like C2-type domain (IgC2, characterized by an overall β-strand topology and several disulfide bonds);
III. a helical transmembrane domain; and
IV. a topological (cytoplasmic) domain, containing immunoreceptor tyrosine-based switch motifs (ITSMs), which are docking sites for the SH2 domain of SLAM-associated protein (SAP) and the related Ewing's sarcoma-associated transcript. ITSM motifs carry the consensus sequence TxYxxV/I/L that have overlapping specificity for activating and inhibitory binding partners.

For example, in human NTB-A (e.g. accession no. Q96DU3, isoform 1), the signal peptide has been identified to be located at positions 1-21, the ectodomain has been identified to be located at positions 22-226 (wherein IgV was located at positions 35-120 and IgC2 at positions 132-209), the transmembrane domain was located at positions 227-247, and the cytoplasmic (intracellular) domain—at positions 248-331.

The terms "NTB-A ectodomain" "sNTB-A" and "seSLAMF6", used interchangeably herein, refer to the extracellular, surface exposed portion of NTB-A, comprising at least the IgV and the IgC2 domains. Typically and advantageously, an NTB-A ectodomain used in the methods and compositions of the invention substantially excludes other NTB-A domains as described herein, such as the signal peptide, the transmembrane domain and the topological domain. Such an advantageous NTB-A ectodomain polypeptide is referred to herein as an "isolated NTB-A ectodomain". An isolated NTB-A ectodomain is typically and conveniently produced synthetically, e.g. by recombinant methods as described herein. In other words, while isolated NTB-A ectodomain polypeptides may contain residual NTB-A sequences (e.g. 1-10 and preferably 5 or less amino acids), they lack any additional NTB-A structures that function as they would in the intact NTB-A polypeptide.

In particular, the signal peptide is advantageously excluded. As opposed to previous disclosure by Valdez and others, reporting that a polypeptide comprising the extracellular domain of NTB-A including the preceding signal peptide is characterized by NTB-A antagonistic activity (Valdez et al., 2004), the present disclosure demonstrates that an isolated NTB-A ectodomain lacking the signal peptide or additional sequences exhibit potent NTB-A agonistic activity, as well as unexpected therapeutically advantageous properties as described herein.

As detailed herein, NTB-A homotypic engagement initiates signal transduction cascades, in which SAP association is induced or increased and Fyn and Lck are recruited. These events contribute to the production of a tight immune synapse and specific T cell activation, and orient mTOC formation for precise lytic degranulation. Engagement of NTB-A by NTB-A ectodomain is described herein to rescue anti-tumor T cells from activation-induced cell death (AICD) and from ionizing radiation, improve interferon gamma (IFN-γ) production, enhance surface CD137 (4-1BB) expression, reverse T cell apoptosis and enhance tumor cell killing by T cells. Non-limitative examples of methods for determining these activities are presented in the Examples hereinbelow. Thus, an "NTB-A agonistic activity" as used herein refers to the ability to exert a biological activity of a native NTB-A, as described herein.

The phrase "NTB-A ectodomain or an agonist thereof" as used herein thus refers to a molecule as described herein that specifically binds with a cell surface expressed endogenous NTB-A molecule (homotypic binding) to induce a signal transduction pathway characteristic of NTB-A homotypic engagement as described herein, thereby exerting an NTB-A agonistic activity. In some embodiments, the NTB-A ectodomain or an agonist thereof retains at least 70%, at least 80%, at least 90%, at least 95% or 100% of the activity of endogenous NTB-A. In other embodiments, said NTB-A ectodomain or an agonist thereof exerts enhanced agonist activity, e.g. 110%, 120%, 130%, 140% or 150% of native NTB-A. In certain other embodiments, the NTB-A ectodomain agonist may exert an enhanced biological activity of a native NTB-A, e.g. up to 200% of the activity exerted by native NTB-A ectodomain. In other embodiments, the NTB-A ectodomain agonist further comprises an epitope tag (e.g. polyhistidine tag) and/or a plasma half-life elongating moiety. For example, the sNTB-A polypeptide may be fused or conjugated an immunoglobulin or a portion thereof. Other half life elongating substances include biologically suitable polymers or copolymers, for example, a polyalkylene glycol compound, such as a polyethylene glycol or a polypropylene glycol. Other appropriate polyalkylene glycol compounds include, but are not limited to, charged or neutral polymers of the following types: dextran, polylysine, colominic acids or other carbohydrate based polymers, polymers of amino acids, and biotin derivatives.

Other examples of the half-life extending moiety, in accordance with the invention, include a copolymer of ethylene glycol, a copolymer of propylene glycol, a carboxymethylcellulose, a polyvinyl pyrrolidone, a poly-1,3-dioxolane, a poly-1,3,6-trioxane, an ethylene/maleic anhydride copolymer, a polyaminoacid (e.g., polylysine), a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group, an immunoglobulin light chain and heavy chain, an immunoglobulin Fc domain or a portion thereof (see, e.g., U.S. Pat. No. 6,660,843), a CH2 domain of Fc, an albumin (e.g., human serum albumin (HSA)); see, e.g., U.S. Pat. No. 6,926,898 and US 2005/0054051; U.S. Pat. No. 6,887,470), a transthyretin (TTR; see, e.g., US 2003/0195154 A1; 2003/0191056 A1), or a thyroxine-binding globulin (TBG).

It should be understood, that the resulting polypeptide or conjugate is selected such that NTB-A agonistic activity is substantially maintained, as described herein.

In other embodiments, the NTB-A ectodomain agonist is an antibody. The terms "antibody" or "antibodies" as used herein refer to an antibody, preferably a monoclonal antibody, or fragments thereof, including, but not limited to, a full length antibody having a human immunoglobulin constant region, a monoclonal IgG, a single chain antibody, a humanized monoclonal antibody, an F(ab')2 fragment, an F(ab) fragment, an Fv fragment, a labeled antibody, an immobilized antibody and an antibody conjugated with a heterologous compound. Each possibility represents a separate embodiment of the invention. In one embodiment, the antibody is a monoclonal antibody. In another embodiment, the antibody is a polyclonal antibody. In another embodiment, the antibody is a humanized antibody.

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. These include, but are not limited to, the hybridoma technique, the human B-cell hybridoma technique, and the Epstein-Barr virus (EBV)-hybridoma technique. Besides the conventional method of raising antibodies in vivo, antibodies can be generated in vitro using phage display technology, by methods well known in the art (e.g. Current Protocols in Immunology, Colligan et al (Eds.), John Wiley & Sons, Inc. (1992-2000), Chapter 17, Section 17.1).

An antigen (e.g. NTB-A ectodomain) or immunogenic complex (e.g. a NTB-A ectodomain epitope conjugated to a protein carrier such as bovine serum albumin (BSA)) can be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art. The antisera obtained can be used directly (e.g. as diluted sera or as purified polyclonal antibodies), or monoclonal antibodies may be obtained, as described herein.

A monoclonal antibody (mAb) is a substantially homogeneous population of antibodies to a specific antigen. mAbs may be obtained by methods known to those skilled in the art. See, for example U.S. Pat. No. 4,376,110; Ausubel et al ("Current Protocols in Molecular Biology," Volumes I-III, John Wiley & Sons, Baltimore, Md., 1994).

Antibody fragments may be obtained using methods well known in the art. (See, for example, Harlow, E. and Lane, D. (1988). Antibodies: A Laboratory Manual, Cold Spring Harbor Laboratory, New York). For example, antibody fragments according to the present invention can be prepared by proteolytic hydrolysis of the antibody or by expression in E. coli or mammalian cells (e.g., Chinese hamster ovary (CHO) cell culture or other protein expression systems) of DNA encoding the fragment.

An Fv is composed of paired heavy chain variable and light chain variable domains. This association may be non-covalent. Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single-chain Fvs is provided in the literature of the art.

The term "human antibody" includes antibodies having variable and constant regions corresponding substantially to human germline immunoglobulin sequences known in the art. Human antibodies used in embodiments of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. Human antibodies can also be produced using various additional techniques known in the art, including phage-display libraries or other well known methods (e.g. U.S. Pat. No. 5,545,807).

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (e.g. PCT patent applications WO 86/01533, WO 97/02671 and WO 90/07861, and U.S. Pat. Nos. 5,693,762, 5,693,761, and 5,225,539). Additionally, CDR grafting may be performed to alter certain properties of the antibody molecule including affinity or specificity. A non-limiting example of CDR grafting is disclosed in U.S. Pat. No. 5,225,539.

It will be appreciated that for human therapy, humanized antibodies are preferably used. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody.

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed as is known in the art (see, for example: U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species.

After antibodies have been obtained, they may be tested for activity, for example via enzyme-linked immunosorbent assay (ELISA).

In various embodiments, the antibodies of the present invention are anti-sNTB-A antibodies, i.e. Abs that specifically bind to an NTB-A ectodomain. The terms "specific binding" or "specifically binds" refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the association constant KA is higher than $10^6$ $M^{-1}$. If necessary, nonspecific binding can be reduced without substantially affecting specific binding by varying the binding conditions. The appropriate binding conditions, such as concentration of antibodies, ionic strength of the solution, temperature, time allowed for binding, concentration of a blocking agent (e.g., serum albumin, milk casein), etc., may be optimized by a skilled artisan using routine techniques. The term "specifically bind" as used herein may further indicate that the binding of an antibody to an antigen is not competitively inhibited by the presence of non-related molecules. Conveniently, detection of the capacity of an antibody to specifically bind an antigen, e.g. an NTB-A ectodomain, may be performed by quantifying specific antigen-antibody complex formation (e.g. by ELISA).

In other embodiments, the NTB-A ectodomain agonist is a small molecule. A "small molecule" is defined herein to have a molecular weight below about 500 Daltons. Such compounds may include synthetic organic or inorganic compounds, peptides and the like.

Methods of screening compounds for a desired activity, as well as methods for rationally designing molecules interacting with a desired structure, are known in the art.

Synthetic and Recombinant Methods

The polypeptides and peptides of the invention (e.g. NTB-A ectodomain polypeptides and derivatives) may be isolated or synthesized using any recombinant or synthetic method known in the art. For instance, peptides or polypeptide fragments may be synthesized by methods including, but not limited to, solid phase (e.g. Boc or f-Moc chemistry) and solution phase synthesis methods. For example, peptides can be synthesized by a solid phase peptide synthesis method of Merrifield (1963, J Am Chem Soc 85, 2149). Alternatively, a peptide can be synthesized using standard solution methods well known in the art (see, for example, Bodanszky, 1984) or by any other method known in the art for peptide synthesis.

Polypeptides and peptides may conveniently be produced by recombinant technology. Recombinant methods for designing, expressing and purifying proteins and peptides are known in the art (see, e.g. Sambrook et al., 1989, 1992, 2001, Molecular Cloning: A Laboratory Manual, Cold Springs Harbor Laboratory, New York). Nucleic acid molecules may include DNA, RNA, or derivatives of either DNA or RNA. An isolated nucleic acid sequence encoding a polypeptide or peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide. A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Polynucleotides that include more or less nucleotides can result in the same or equivalent proteins. Using recombinant production methods, selected host cells, e.g. of a microorganism such as *E. coli* or yeast, are transformed with a hybrid viral or plasmid DNA vector including a specific DNA sequence coding for the polypeptide or polypeptide analog and the polypeptide is synthesized in the host upon transcription and translation of the DNA sequence.

In various embodiments, the sequences may be derived directly from the corresponding sequence of the receptor (such that they may be identical to a portion of a sequence of the receptor) or may contain certain derivatizations and substitutions. Thus in some embodiments the use of salts and functional derivatives of these sequences are contemplated, as long as they retain the respective biologic functions, as detailed herein. Accordingly the present invention encompasses peptide homologs containing non-natural amino acid derivatives or non-protein side chains. The peptide homologs of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. Generally, any pharmaceutically acceptable salt of peptides may be used, as long as its biological activities are maintained.

The amino acid residues described herein are preferred to be in the "L" isomeric form. However, residues in the "D" isomeric form can be substituted for any L-amino acid residue, as long as the peptide substantially retains the desired functional property.

Chemical derivatives may have one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and omithine may be substituted for lysine.

In addition, a derivative can differ from the natural sequence of the polypeptides or peptides of the invention by chemical modifications including, but are not limited to, terminal-$NH_2$ acylation, acetylation, or thioglycolic acid amidation, and by terminal-carboxlyamidation, e.g., with ammonia, methylamine, and the like.

In another aspect, the methods of the invention may be affected by expressing in a cell population obtained from a subject an isolated polypeptide comprising an NTB-A ectodomain (e.g. by isolating T cells from a subject, introducing a vector capable of expressing an isolated NTB-A ectodomain and re-introducing the cells into the subject, such that the polypeptide is secreted in the subject and is capable of contacting the subject's T cells). Thus, for example, a method for reducing or inhibiting T cell death, may be affected by contacting T cells with a therapeutically effective amount of an NTB-A ectodomain or an agonist thereof, wherein said NTB-A ectodomain is produced in vivo by gene therapy methods.

The preparation of expression constructs or vectors used for delivering and expressing a desired gene product are known in the art. Such construct typically comprise regulatory sequences or selectable markers, as known in the art. The nucleic acid construct (also referred to herein as an "expression vector") may include additional sequences that render this vector suitable for replication and integration in prokaryotes, eukaryotes, or optionally both (e.g., shuttle vectors). In addition, a typical cloning vector may also contain transcription and translation initiation sequences, transcription and translation terminators, and a polyadenylation signal.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Strategene, pTRES which is available from Clontech, and their derivatives. These may serve as vector backbone for the constructs useful in embodiments described herein.

Recombinant viral vectors are useful for in vivo expression of the genes of the present invention since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Ex Vivo Expansion and Cell Preparations

Thus, according to a first aspect of the invention, there is provided an improved method for preparing a cell composition, comprising the step of incubating ex vivo a T cell containing cell population with a therapeutically effective amount of an isolated (e.g. recombinantly produced) polypeptide comprising an NTB-A ectodomain or an agonist thereof. Typically, the method comprises the step of incubating ex vivo a T cell containing cell population with an effective amount of an isolated NTB-A ectodomain or an agonist thereof, as detailed herein.

T lymphocytes (T cells) are one of a variety of distinct cell types involved in an immune response. The activity of T cells is regulated by antigen, presented to a T cell in the context of a major histocompatibility complex (MHC) molecule. The T cell receptor (TCR) then binds to the MHC-antigen complex. Once antigen is complexed to MHC, the MHC-antigen complex is bound by a specific TCR on a T cell, thereby altering the activity of that T cell. Proper activation of T lymphocytes by antigen-presenting cells requires stimulation not only of the TCR, but the combined and coordinated engagement of its co-receptors.

T helper cells (TH cells) assist other white blood cells in immunologic processes, including maturation of B cells into plasma cells and memory B cells, and activation of cytotoxic T cells and macrophages. These cells are also known as $CD4^+$ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response.

Cytotoxic T cells ($T_C$ cells, or CTLs) destroy virus-infected cells and tumor cells, and are also implicated in transplant rejection. These cells are also known as $CD8^+$ T cells since they express the CD8 glycoprotein at their surfaces. These cells recognize their targets by binding to antigen associated with MHC class I molecules, which are present on the surface of all nucleated cells.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress autoreactive T cells that escaped the process of negative selection in the thymus.

The TCR is a complex of integral membrane proteins, wherein stimulation by specific MHC-presented antigen recognition and binding by the clonotype-specific α/β heterodimer leads to activation of transcription and subsequent proliferation and effector functions (such as cytotoxic activity in $CD8^+$ T cells and cytokine secretion in $CD4^+$ T cells). This activation involves other subunits of the receptor complex as detailed below that couple the extracellular liganding event to downstream signaling pathways such as protein phosphorylation, the release of inositol phosphates and the elevation of intracellular calcium levels.

The intracellular portions of the CD3 γ, δ, ζ and subunits contain copies of a sequence motif termed ITAMs (immunoreceptor tyrosine-based activation motifs). ITAMs can serve as protein tyrosine kinase substrates and, after phosphorylation, as binding sites for SH2 domains of yet other kinases. The regulation and mechanism of the recruitment of protein kinases to the activated T cell receptor involves members of both the Syk family (ZAP-70) and Src family (Lck) of kinases.

TCR stimulation as detailed above may be antigen-specific or antigen non-specific (Polyclonal). Suitable antigen-specific TCR activators include antigens bound to MHC molecules, typically in the context of antigen presenting cells (APC). Polyclonal TCR activators are capable of initiating the signal transduction and transcriptional activation pathways associated with specific TCR engagement in the absence of specific antigens. Suitable polyclonal T cell activators include antibodies that bind and crosslink the T cell receptor/CD3 complex, e.g. subunits as described herein. Exemplary antibodies that crosslink the T cell receptor include the HIT3a, UCHT1 and OKT3 monoclonal antibodies. The stimulation is provided at an amount and under conditions as known in the art so as to induce the above mentioned functional effects. Various non-limitative examples for TCR stimulation (both antigen-specific and polyclonal) are provided in the Examples hereinbelow.

In another embodiment, the population comprises $CD8^+$ T cells. In another embodiment, the T cells are $CD8^+$ T cells. In another embodiment, the cells are genetically engineered or modified (e.g. to exert a desired antigen specificity). For example, in another embodiment, the cells are lymphocytes (e.g. purified T cells such as CTL) genetically engineered to express a TCR pre-designed to re-direct them against cancer cells or against pathogens (e.g. viruses). By means of a non-limitative example, T cells engineered to express a TCR directed against NY-ESO-1, an antigen expressed on many solid tumors, e.g. synovial sarcoma. In another embodiment, the cells are peripheral blood mononuclear cells genetically engineered to express a chimeric antigen receptor (CAR) to re-direct them against cancer cells or pathogens. For example, without limitation, CAR-T cells targeting CD19 may be used for the treatment of B cell malignancies such as acute lymphoblastic leukemia. In another embodiment, the cells are peripheral blood mononuclear cells genetically engineered to express genes that enhance their biological function. For example, without limitation, such genes may include membrane bound cytokine and cytokine receptor (e.g. IL-2 and IL-2R). Certain additional non-limitative examples for the use of genetically modified cells, expressing a TCR directed against the tumor associated antigen $gp100_{25-33}$ or co-stimulatory molecules such as 4-1BBL, are described in the Examples below.

In another embodiment the population comprises $CD4^+$ T cells. In another embodiment the population comprises Myeloid Cells. In another embodiment the population comprises a combination of $CD8^+$ T cells, $CD4^+$ T cells and Myeloid Cells.

In another embodiment, incubation with the NTB-A ectodomain polypeptide or agonist is performed in an amount and under conditions sufficient to induce or up-regulate activation markers and/or cytokines associated with T cell activation (e.g. Tc1 activation markers such as IFN-γ). Advantageously, the incubation with the NTB-A ectodomain polypeptide or agonist is performed so as to up-regulate CD137 expression on T cells. Such exemplary advantageous conditions are specified below.

Thus, according to certain advantageous embodiments, the incubation is performed in the presence of T cell receptor (TCR) stimulation. In other embodiments, TCR stimulation may be antigen non-specific (performed, for example, using antibodies specific to CD3 that activate the receptor upon binding, e.g. OKT3) or antigen-specific (using suitable antigen presenting cells and antigen).

In the context of cancer treatment, antigen-specific stimulation typically employs stimulation to tumor associated antigens. The term "tumor-associated antigen" (TAA) refers to any protein, peptide or antigen associated with (carried by, expressed by, produced by, secreted by, etc) a tumor or tumor cell(s). Tumor-associated antigens may be (nearly) exclusively associated with a tumor or tumor cell(s) and not with healthy normal cells or may be over expressed (e.g., 2 times, 5 times, 10 times, 50 times, 100 times, 1000 times or more) in a tumor tissue or tumor cell(s) compared to healthy normal tissue or cells. More particularly, a TAA is an antigen capable of being presented (in processed form) by MHC determinants of the tumor cell. Hence, tumor-associated antigens are likely to be associated only with tumors or tumor cells expressing MHC molecules. Non-limitative examples of well known TAA are MART-1, $gp100_{209-217}$, $gp100_{154-163}$, CSPG4, NY-ESO, MAGE-A1, Tyrosinase.

According to certain additionally advantageous embodiments, incubation is performed in the presence of feeder cells (e.g.).

The term "feeder cells" generally refers to cells of one type that are co-cultured with cells of a second type, to provide an environment in which the cells of the second type can be maintained and proliferated. The feeder cells can be from a different species than the cells they are supporting. For the purpose of the present invention, this term specifically refers to Fc receptor-bearing accessory cells, which are typically allo-reactive with the T cell containing population to be propagated. In other words, the feeder cells need not be histocompatible with the T-cell containing population to be propagated, and in certain advantageous embodiments the two populations typically HLA-mismatched. A typical example of feeder cells used in embodiments of the invention is allogeneic normal donor peripheral blood mononuclear cells, PBMC. Typically and advantageously, the use of such feeder cells is performed in conjunction with antigen non-specific TCR stimulation, e.g. by incubation with antigen non-specific stimulating antibodies, as detailed herein.

According to further advantageous embodiments, TIL compositions for adoptive cell therapy are prepared with irradiated PBMC (incapable of proliferation). For example, PBMC may conveniently be attenuated by irradiation by exposing the cells to 6000RAD. In another embodiment, TIL compositions for adoptive cell therapy are prepared with artificial antigen presenting entities including antigen presenting cells and inert particles carrying antigens, to provide antigen-specific stimulation.

The polypeptides of the invention have been demonstrated to be unexpectedly superior to IL-2, in producing safer and more effective T cell activation. Thus, the use of IL-2 may be substantially reduced and even completely replaced by the polypeptides of the invention. Accordingly, in another embodiment, the incubation is advantageously performed without the addition of exogenous IL-2. Without wishing to be bound by a specific theory or mechanism of action, embodiments of the invention are directed to such improved cell compositions, in which effector T cell activity (e.g. CTL activity) is expanded while regulatory T cell activity is minimized.

In another embodiment, the incubation is performed with the addition of exogenous IL-2 ranging from 300-6000 IU/ml. In another embodiment, incubation is performed in the presence of exogenous CD137 ligand or an agonist thereof.

As used herein the term "endogenous" means that the molecule has been produced or synthesized from within an organism or a tissue or a cell. The term "exogenous" means that this antigen or enhancing molecule has been introduced from outside of the cell or tissue.

For example, without limitation, TIL compositions may be obtained by incubation of TIL (or T cells as described herein) with PBMC at a ratio of TIL to PBMCs of 200:1 to 1:300, e.g. 1:200 to 1:100, in the presence of anti-CD3 antibodies at 1 ng/ml-1 µg/ml, preferably 10-100 ng/ml (e.g. 30 ng/ml of the OKT3 antibody), and 1-200 µg/ml, preferably 10-50 µg/ml, NTB-A ectodomain polypeptide. Incubation may be performed for 3-15 days, preferably 8-12 days. Additional methods and protocols for producing cell compositions are exemplified in the Examples section herein.

According to certain protocols, TILs obtained from a patient's tumor may be cultured ex-vivo prior to the step of REP expansion as described above. For example, TIL may be pre-cultured for up to 28 days in the presence of IL-2 (e.g. 300-6,000 IU/ml), prior to addition of anti-CD3 antibodies and feeder cells. According to various embodiments, the NTB-A ectodomain polypeptides of the invention may be further supplemented at this preliminary culture step e.g. at 10-50 µg/ml (with or without IL-2) and the T cell response may be monitored.

In some embodiments, the resulting TIL composition may be administered to a subject in need thereof at $10^8$ to $10^{12}$ or in other embodiments $10^6$ to $10^{12}$ cells per patient, e.g. $10^{10}$ or $10^6$ cells/patient.

In various embodiments, the methods of the invention provide for T cell propagation and expansion. According to particular embodiments, incubation with the NTB-A ectodomain or agonist is performed so as to enhance the number of T cells by at least twofold, at least 4 fold, at least 8 fold, at least 10 fold, at least 50 fold or at least 100 fold. According to certain embodiments, e.g. when an improved REP protocol is employed, incubation with the NTB-A ectodomain or agonist typically results with the number of T cells being enhanced by at least 200 fold, at least 500 fold, at least 1000 fold, at least 2000 fold, at least 5000 fold, at least 7000 fold or at least 10,000 fold. Each possibility represents a separate embodiment of the invention.

In another aspect, there is provided a cell composition prepared by the methods of the invention. In another embodiment, the cell composition is suitable for adoptive transfer into a recipient subject in need thereof. As used herein, and unless otherwise specified, the term "adoptive transfer" refers to a form of passive immunotherapy where previously sensitized immunologic agents (e.g., cells or serum) are transferred to the recipients.

The phrases "adoptive transfer immunotherapy", "adoptive cell therapy" and "adoptive cell immunotherapy" are used interchangeably herein to denote a therapeutic or prophylactic regimen or modality, in which effector immunocompetent cells, such as the cell compositions of the invention, are administered (adoptively transferred) to a subject in need thereof, to alleviate or ameliorate the development or symptoms of cancer or infectious diseases.

The cell composition may comprise a T cell-containing population in an effective amount. For example, an amount effective for adoptive transfer immunotherapy is an amount sufficient to induce or enhance a beneficial immune response such as an anti-tumor response, e.g. $10^6$ to $10^{12}$ cells. It is to be understood, that while cell preparations suitable for in vivo administration, particularly for human subjects, may contain pharmaceutically acceptable excipients or diluents, such preparations are sufficiently devoid of contamination by pathogens, toxins, pyrogens and any other biological and non-biological agents which are not recognized to be pharmaceutically acceptable. For example, without limitation, T cells for adoptive transfer immunotherapy may conveniently be suspended in an injection suitable buffer that contains sterile saline with 2% human albumin, and optionally IL-2 (e.g. 300 IU/ml).

According to certain preferable embodiments, the cell composition is histocompatible with the subject to be treated (e.g. autologous cells or MHC II-matched allogeneic cells).

The term "histocompatibility" refers to the similarity of tissue between different individuals. The level of histocompatibility describes how well matched the patient and donor are. The major histocompatibility determinants are the human leukocyte antigens (HLA). HLA typing is performed between the potential donor and the potential recipient to determine how close a HLA match the two are. The term "histocompatible" as used herein refers to embodiments in which all six of the HLA antigens (2 A antigens, 2 B antigens and 2 DR antigens) are the same between the donor and the recipient.

However, in other embodiments, donors and recipients who are "mismatched" at two or more antigens, for example 5 of 6, or in other embodiments, 4 of 6 or 3 of 6 match, may be encompassed by certain embodiments of the invention, despite the donor and recipient not having a complete match. The term "substantially histocompatible" as used herein refers to embodiments in which five out of six of the HLA antigens are the same between the donor and the recipient.

Thus, according to some embodiments, the invention relates to a method comprising:
  i) obtaining a T cell containing population from a subject in need thereof (or from a donor histocompatible or substantially histocompatible with the subject),
  ii) incubating a T cell containing cell population ex vivo with an effective amount of an isolated NTB-A ectodomain or an agonist thereof, and
  iii) administering the resulting T cell containing cell population to said subject.

According to other embodiments, the invention relates to a method for treating cancer in a subject in need thereof, comprising:
  i) obtaining a T cell containing population from the subject (or from a donor histocompatible with the subject),
  ii) incubating a T cell containing cell population ex vivo with an effective amount of an isolated NTB-A ectodomain or an agonist thereof (e.g. so as to up-regulate CD137 expression on the T cells), and
  iii) administering the resulting T cell containing cell population to said subject (e.g. so as to induce or enhance an anti-tumor immune response), thereby treating cancer in said subject.

According to other embodiments, the invention relates to a method for treating a T cell mediated pathology in a subject in need thereof, comprising:
  i) obtaining a T cell containing population from the subject (or from a donor histocompatible with the subject),
  ii) incubating a T cell containing cell population ex vivo with an effective amount of an isolated NTB-A ectodomain or an agonist thereof (e.g. so as to up-regulate CD137 expression on the T cells), and
  iii) administering the resulting T cell containing cell population to said subject, thereby treating cancer in said subject.

According to various beneficial embodiments, step ii) is performed in the presence of antigen stimulation and/or according to the methods and protocols described herein.

Pharmaceutical Compositions, Kits and Therapeutic Combinations

In other embodiments, the NTB-A ectodomain and agonists thereof used in the methods of the invention are provided in the form of a pharmaceutical composition, optionally further comprising a pharmaceutically acceptable carrier, excipient or diluents.

Said compositions may be in any pharmaceutical form suitable for administration to a patient, including but not limited to solutions, suspensions, lyophilized powders for reconstitution with a suitable vehicle or dilution prior to usage, capsules, tablets, sustained-release formulations and the like. The compositions may comprise a therapeutically effective amount of an agent of the present invention, preferably in purified form, and a pharmaceutical excipient. As used herein, "pharmaceutical excipient" includes solvents, dispersion media, coatings, antibacterial and antifungal agents, isotonic and absorption delaying agents etc. and combinations thereof, which are compatible with pharmaceutical administration. Hereinafter, the phrases "therapeutically acceptable carrier" and "pharmaceutically acceptable carrier", which may be used interchangeably, refer to a carrier or a diluent that does not cause significant irritation to an organism and does not abrogate the biological activity and properties of the administered compound. The compositions may also contain other active compounds providing supplemental, additional, or enhanced therapeutic functions. In another embodiment, the composition consists essentially of a NTB-A ectodomain or agonist thereof and one or more pharmaceutical excipients. In another embodiment, the composition consists of a NTB-A ectodomain or agonist thereof and one or more pharmaceutical excipients. Each possibility represents a separate embodiment of the invention.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes. A pharmaceutical composition of the invention is formulated to be compatible with its intended route of administration. Methods to accomplish the administration are known to those of ordinary skill in the art. Examples of suitable excipients and modes for formulating the compositions are described in the latest edition of "Remington's Pharmaceutical Sciences" by E. W. Martin.

Pharmaceutical compositions according to the invention (e.g. containing NTB-A ectodomain or agonist thereof) are typically liquid formulations suitable for injection or infusion. Examples of administration of a pharmaceutical composition include oral ingestion, inhalation, intravenous and continues infusion, intraperitoneal, intramuscular, intracavity, subcutaneous, cutaneous, or transdermal administration. According to certain particular embodiments, the compositions are suitable for intralesional (e.g. intratumoral) administration. In other embodiments, the compositions are suitable for intravenous administration.

For example, saline solutions and aqueous dextrose and glycerol solutions can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Solutions or suspensions used for intravenous administration typically include a carrier such as physiological saline, bacteriostatic water, Cremophor EL™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin. Where necessary, the composition may also include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Oral compositions include an inert diluent or edible carrier. The composition can be enclosed in gelatin or compressed into tablets. For the purpose of oral administration, the active agent can be incorporated with excipients and placed in tablets, troches, or capsules. Pharmaceutically compatible binding agents or adjuvant materials can be included in the composition. The tablets, troches, and capsules, may optionally contain a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; or a sweetening agent or a flavoring agent.

The composition may also be administered by a transmucosal or transdermal route. For example, antibodies that comprise an Fc portion may be capable of crossing mucous membranes in the intestine, mouth, or lungs (via Fc receptors). Transmucosal administration can be accomplished through the use of lozenges, nasal sprays, inhalers, or suppositories. Transdermal administration can also be accomplished through the use of a composition containing ointments, salves, gels, or creams known in the art. For transmucosal or transdermal administration, penetrants appropriate to the barrier to be permeated are used. For administration by inhalation, the antibodies are delivered in an aerosol spray from a pressured container or dispenser, which contains a propellant (e.g., liquid or gas) or a nebulizer. The composition can be formulated as a suppository, with traditional binders and carriers such as triglycerides.

Solutions or suspensions used for intradermal or subcutaneous application typically include at least one of the following components: a sterile diluent such as water, saline solution, fixed oils, polyethylene glycol, glycerin, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

In certain embodiments, polypeptide active agents (e.g. NTB-A ectodomain or agonist thereof) are prepared with carriers to protect the polypeptide against rapid elimination from the body. Biodegradable polymers (e.g., ethylene vinyl acetate, polyanhydrides, polyglycolic acid, collagen, polyorthoesters, and polylactic acid) are often used. Methods for the preparation of such formulations are known by those skilled in the art. Liposomal suspensions can be used as pharmaceutically acceptable carriers too. The liposomes can be prepared according to established methods known in the art (U.S. Pat. No. 4,522,811). In other particular embodiments, liposomes containing PEG moieties or glycolipids may advantageously be used to enhance blood plasma retention and/or to reduce liver uptake.

In some embodiments, larger liposomes (e.g. 300 nm or more) are used, which mediate uptake and clearance preferentially by the spleen and having reduced liver clearance. In other embodiments, smaller liposomes (e.g. 40 nm or less) are used, which preferentially mediate liver uptake and clearance. In yet other embodiments, liposomes of 40-300 nm are used, which may have enhanced blood plasma retention. In other embodiments, the liposomes may further contain polymers such as PEG (see, for example, Litzinger et al., Biochim Biophys Acta. 1994 Feb. 23; 1190(1):99-107). US 2011160642 discloses pegylated liposomal formulations having reduced accumulation in the liver and spleen. A range of liposomes formulated to evade uptake by the reticuloendothelial system and circulate for longer are described in U.S. Pat. No. 6,284,267.

In addition, the NTB-A ectodomain or agonist of the present invention may be administered with various effector molecules such as heterologous polypeptides, drugs, radionucleotides, or toxins. Thus, in some embodiments, the NTB-A ectodomain or agonist may be administered in combination (concurrent or sequential) with a cancer treatment, e.g. radiation or chemotherapy.

Continuous as well as intermittent intravenous administration can also be achieved using an implantable or external pump (e.g., INFUSAID pump). The use of such pumps and adjustment of dosing protocols to the required parameters are well within the abilities of the skilled artisan.

In another embodiment, administration or addition of the NTB-A polypeptides or agonists of the invention may advantageously be performed in combination (concurrent or sequential) with administration of a CD137 ligand (e.g. human CD137 ligand or the extracellular portion thereof) or an agonist thereof (such as an anti-CD137 antibody that induces a biological function associated with activation of CD137 with its cognate ligand). Non-limitative examples of such anti-CD137 antibodies which are commercially available or under clinical investigation include e.g. Bristol Myers Squibb (BMS; Princeton, N.J.) Catalog Number 663513, fully humanized IgG4 monoclonal antibody which may be used e.g. at 10-20 ng/ml, and R&D Systems Catalog Number AF838 polyclonal goat anti-4-1BB which may be used e.g. at 20-40 ng/ml. An amino acid sequence of human CD137 may be found in accession number Q07011. For example, full length human CD137 may have the following amino acid sequence:

```
                                      (SEQ ID NO: 4)
MGNSCYNIVA TLLLVLNFER TRSLQDPCSN CPAGTFCDNN

RNQICSPCPP NSFSSAGGQR TCDICRQCKG VFRTRKECSS

TSNAECDCTP GFHCLGAGCS MCEQDCKQGQ ELTKKGCKDC

CFGTFNDQKR GICRPWTNCS LDGKSVLVNG TKERDVVCGP
```

-continued

```
SPADLSPGAS SVTPPAPARE PGHSPQIISF FLALTSTALL

FLLFFLTLRF SVVKRGRKKL LYIFKQPFMR PVQTTQEEDG

CSCRFPEEEE GGCEL.
```

An amino acid sequence of human CD137 ligand may be found in accession no. NP_003802.1. For example, human CD137 ligand (extracellular portion) may have the following amino acid sequence:

```
                                      (SEQ ID NO: 5)
MREGPELSPD DPAGLLDLRQ GMFAQLVAQN VLLIDGPLSW

YSDPGLAGVS LTGGLSYKED TKELVVAKAG VYYVFFQLEL

RRVVAGEGSG SVSLALHLQP LRSAAGAAAL ALTVDLPPAS

SEARNSAFGF QGRLLHLSAG QRLGVHLHTE ARARHAWQLT

QGATVLGLFR VTPEIPAGLP SPRSE.
```

In another aspect, there is provided a therapeutic combination comprising 1) an NTB-A ectodomain or an agonist thereof, 2) an isolated polypeptide comprising CD137 ligand or an agonist thereof and optionally 3) a pharmaceutically acceptable carrier. In another embodiment the combination comprises human NTB-A ectodomain. In another embodiment the combination comprises human CD137 ligand. In another embodiment the agonist is an antibody (e.g. NTB-A specific or CD137 specific).

In another embodiment, administration or addition of the NTB-A polypeptides or agonists of the invention may be performed in combination (concurrent or sequential) with administration of other immune modulators, e.g. signaling receptor-targeting reagents exhibiting a modifying effect on immune cell function. Examples for such reagents include e.g. antagonists or inhibitors (such as antibodies) of CTLA-4, PD-1 or PD-L1. Non-limitative examples for antibodies which are commercially available or under clinical investigation include CTLA-4 blocking antibody (YERVOY™, BMS, approved for use in the clinic at 1-3 mg/kg), PD-1 blocking antibodies (KEYTRUDA™, Merck, 0.5-2 mg/kg; OPDIVO™, BMS, 1-3 mg/kg), and PD-L1 targeting antibodies (ROCHE, under clinical investigation).

In another aspect, there is provided a therapeutic combination comprising 1) an NTB-A ectodomain or an agonist thereof, 2) an immune modulator and optionally 3) a pharmaceutically acceptable carrier.

In another embodiment the combination comprises human NTB-A ectodomain. In another embodiment the combination comprises antagonists or inhibitors of CTLA-4, PD-1 or PD-L1. In another embodiment the agonist is an antibody (e.g. NTB-A specific, CTLA-4 specific, PD-1 specific or PD-Llspecific).

According to other aspects, the invention is directed to a kit containing a polypeptide comprising an NTB-A ectodomain or an agonist thereof, and instructions to use the polypeptide in the methods of the invention.

In another embodiment the composition is not administered in the form of a vaccine further comprising an additional antigen. In another embodiment the composition is not administered by a therapeutic regimen adapted for vaccination. Vaccines and vaccination protocols are well known in the art. Vaccines typically contain one or more antigens to which a desired immune response is to be elicited (e.g. attenuated cancer cells or tumor associated antigens), and often contain additional adjuvants, used to boost or enhance the immune response (e.g. Alum. Or mineral oil).

For example, without limitation, a suitable dose range for an NTB-A containing polypeptide or agonist of the invention may be from 0.1 mg/kg to 20 mg/kg administered every 7 to 90 days between doses. It is to be understood that the treatment may be maintained or adjusted by the treating physician to maintain clinical benefit and avoid limiting toxicities of the overall treatment program.

Subjects and Therapeutic Use

According to certain embodiments of the invention, there is provided a cell composition prepared by a method comprising the step of incubating a T cell containing cell population ex vivo with a therapeutically effective amount of an isolated NTB-A ectodomain or an agonist thereof, for use in treating cancer in a subject in need thereof.

According to certain other embodiments of the invention, there is provided a pharmaceutical composition comprising a therapeutically effective amount of an isolated NTB-A ectodomain or an agonist thereof, for use in treating cancer in a subject in need thereof.

According to certain additional embodiments of the invention, there is provided a pharmaceutical composition comprising a therapeutically effective amount of an isolated NTB-A ectodomain or an agonist thereof, for use in reducing or inhibiting T cell death.

According to certain further embodiments of the invention, there is provided a pharmaceutical composition comprising a therapeutically effective amount of an isolated NTB-A ectodomain or an agonist thereof, for use in treating or preventing cytopenia in a subject in need thereof.

In various embodiments, the composition and use thereof are as detailed herein.

In another aspect, there is provided a method of treating cancer in a subject in need thereof, comprising administering to the subject a cell composition of the invention, thereby treating cancer in said subject. According to other embodiments, the cell compositions of the invention may be used for the treatment of various other T cell dependent pathologies and conditions, i.e. conditions which may be alleviated by a beneficial T cell response. For example, without limitation, various tumors and infections (e.g. viral) are manifested by characteristic T cell epitopes, such as CTL epitopes. Specific activation and propagation of T cells directed to these epitopes according to the methods of the invention may be beneficial for treating such conditions.

The compositions of the present invention are intended in various embodiments for the treatment of a proliferative disorder, specifically, a malignant disorder. As used herein to describe the present invention, "proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the compositions and methods of the present invention may be used in the treatment of non-solid and solid tumors. The term "cancer" or "cancer cell" is used herein to denote a tissue or cell found in a neoplasm which possesses characteristics which differentiate it from normal tissue or tissue cells.

According to certain preferable embodiments of the methods of the invention, the cell composition is histocompatible with the subject (e.g. autologous cells or MHC II-matched allogeneic cells).

In another aspect, there is provided a method of treating cancer in a subject in need thereof, comprising administering to the subject a therapeutically effective amount of an NTB-A ectodomain or an agonist thereof, thereby treating cancer in said subject.

In another aspect, there is provided a method of treating a T cell dependent pathology in a subject in need thereof, comprising administering to the subject a therapeutically effective amount of an NTB-A ectodomain or an agonist thereof, thereby treating the T cell dependent pathology in said subject.

An "effective amount" or "therapeutically effective amount" refers to an amount sufficient to exert a beneficial outcome in a method of the invention. More specifically, a therapeutically effective amount means an amount of active ingredients (e.g., NTB-A ectodomain or effector cells) effective to prevent, alleviate, or ameliorate symptoms of a disorder (e.g., cancer) or prolong the survival of the subject being treated. In the context of in vitro cell culture methods, an effective amount of an NTB-A ectodomain or agonist thereof is an amount sufficient to exert an agonist NTB-A activity, including, but not limited to T cell expansion, up-regulation of activation markers (e.g. CD137) and reduction of activation-induced T cell death.

Determination of a therapeutically effective amount is well within the capability of those skilled in the art, especially in light of the detailed disclosure provided herein. For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition (See, e.g., Fingl, E. et al. (1975), "The Pharmacological Basis of Therapeutics," Ch. 1, p. 1.).

In another embodiment, the subject to be treated by the methods of the invention is afflicted with a tumor characterized by lack of substantial NTB-A surface expression. In another embodiment, the tumor is not characterized by NTB-A over-expression. In another embodiment, the tumor is a solid tumor. In another embodiment, the subject is afflicted with a tumor characterized by surface expression of CD137. In another embodiment, the cancer is selected from the group consisting of melanoma, urinary tract cancer, gynecological cancer, head and neck carcinoma, primary brain tumor, bladder cancer, liver cancer, lung cancer, breast cancer, ovarian cancer, prostate cancer, cervical cancer, colon cancer and other cancers of the intestinal tract, bone malignancies, connective and soft tissue tumors, and skin cancers. In another embodiment, the cancer is selected from the group consisting of melanoma, bladder cancer, liver cancer, lung cancer, breast cancer, ovarian cancer, prostate cancer, cervical cancer and colon cancer. In another embodiment, the cancer is selected from the group consisting of bladder cancer, liver cancer, lung cancer, breast cancer, ovarian cancer, prostate cancer, cervical cancer and colon cancer. In a particular embodiment, the cancer is melanoma. In another particular embodiment, the cancer is other than melanoma. In another particular embodiment, the cancer is other than a hematopoietic tumor. Each possibility represents a separate embodiment of the invention.

The terms "substantial" and "substantially" as used with respect to surface expression of receptors and polypeptide markers, represents expression in an amount detectable by conventional methods such as immunoassays. In certain embodiments, a tumor characterized by lack of substantial NTB-A surface expression means a tumor in which the amount of NTB-A detected on the surface of the tumor cell is does not exceed 10%, and preferably is below 5%, more preferably below 1%, most preferably below 0.5% of the amount characteristic of endogenously expressing NTB-A, such as lymphocytes.

In another embodiment, the subject has further received or is receiving an adoptive immunotherapy, e.g. a T cell containing composition of the invention.

In another embodiment, the subject is a cytopenic subject, or a subject at risk of developing cytopenia (due to e.g. irradiation or chemotherapy). In another embodiment, the subject is afflicted with or at risk of developing lymphocytopenia. In another embodiment, the subject is not afflicted with an active infectious disease, or with an acute or pathological inflammation. In another embodiment the subject is not afflicted with X-linked lymphoproliferative disease (XLP). In another embodiment, the subject is not afflicted with an autoimmune disease. Each possibility represents a separate embodiment of the invention.

The polypeptides of the invention have been demonstrated to be unexpectedly superior to IL-2, in producing safer and more effective T cell activation. Thus, the use of IL-2 may be substantially reduced and even completely replaced by the polypeptides of the invention. Accordingly, in another embodiment, the methods of the invention are affected without the addition of exogenous IL-2 (in vivo and/or ex vivo). In another embodiment, the use of IL-2 may be reduced by at least 50%, at least 60%, at least 70%, at least 80% and preferably at least 90%.

For instance, IL-2 (Proleukin®) is currently indicated for cancer immunotherapy e.g. at a 600,000 International Units/kg (0.037 mg/kg) dose administered every 8 hours by a 15-minute intravenous infusion for a maximum of 14 doses; a standard dose for expanding T cells in vitro is e.g. 6000 U/ml. According to embodiments of the invention, reduced IL-2 levels may be used as detailed herein. For instance, without limitation, the examples below demonstrate the successful reduction of IL-2 used in cell culture from 6000 U/ml to 300 U/ml, i.e. to 20% of the standard dose. In certain particular embodiments, the methods of the invention may be employed using no more than 1000 U/ml IL-2, or in other embodiments no more than 800, 600, 400, 300 or 200 U/ml exogenously added IL-2 in vitro.

In another aspect, the invention provides a method of reducing or inhibiting T cell death, comprising contacting T cells with a therapeutically effective amount of an isolated polypeptide comprising an NTB-A ectodomain or an agonist thereof.

In another embodiment, the contacting is performed in vitro (e.g. ex vivo). In another embodiment, the contacting is performed in vivo. In another embodiment, the method may be used for reducing or inhibiting T cell death in a subject suffering from or at risk of developing cytopenia. In another embodiment, the method is used for reducing or inhibiting T cell death following administration of T cells to a recipient subject in need thereof.

In another embodiment, the subject is a cytopenic subject, or a subject at risk of developing cytopenia (due to e.g. irradiation or chemotherapy). In another embodiment, the subject is afflicted with or at risk of developing lymphocytopenia. In other embodiments, the subject is not afflicted with an active infectious disease, or with an acute or pathological inflammation. In another embodiment the subject is not afflicted with X-linked lymphoproliferative disease (XLP).

In another aspect, there is provided a method of treating or preventing cytopenia in a subject in need thereof, comprising administering to the subject a therapeutically effective amount of an NTB-A ectodomain or an agonist thereof, thereby treating or preventing cytopenia in said subject.

The term "cytopenia" as used herein refers to a reduction of cellular elements in the circulating blood. Cytopenia may result from a variety of causes, and include both a general reduction of cell numbers in the blood as well as a specific reduction of a particular cell type, such as leukocyte reduction in leukopenia. Leukopenia is a reduction in the circulating white blood cells (WBC) count to <4000/μL. It is usually characterized by a reduced number of circulating neutrophils, although a reduced number of lymphocytes, monocytes, eosinophils, or basophils may also contribute. Thus, immune function is generally greatly decreased. Neutropenia is a reduction in blood neutrophil count. Severe neutropenia is usually defined by an absolute neutrophil count <500/μL. It is more serious when accompanied by monocytopenia and lymphocytopenia. Lymphocytopenia, in which the total number of lymphocytes is <1000/μL in adults, is not always reflected in the total WBC count, because lymphocytes account for only 20 to 40% of the count.

In some embodiments, cytopenia is associated with radiation or chemotherapy. For example, cytopenia may be cytopenia associated with high dose chemotherapy, cytopenia associated with conventional oncology therapy, drug-induced cytopenia, toxin-induced cytopenia and radiation-induced cytopenia. According to other embodiments, cytopenia may be associated with an acquired or congenital immune deficiency that is not associated with an impairment in the NTB-A pathway. Thus, XLP patients are explicitly excluded from these embodiments. For example, the cytopenia may be steroid-induced, induced or exacerbated by an infectious disease (hepatitis, viral disease), or autoimmune-induced (e.g. by systemic lupus erythematosus). In a particular embodiment, the method is used for the treatment or prevention of lymphocytopenia.

In certain other embodiments, the duration of cytopenia may be reduced. For example, the duration of cytopenia may be reduced to below 12 days, preferably below 10 days, more preferably below 8 days and most preferably below 7 days from the onset of treatment. In other embodiments, the duration of cytopenia is reduced to below 5 days, below 4 days, below 3 days, below 2 days or below one day from the onset of treatment. In another embodiment, the methods are useful for reducing the incidence of infection and for increasing survival following chemotherapy or radiation therapy in cancer patients.

Additional Embodiments

Certain exemplary embodiments of the invention are described below.

1. A method for preparing a cell composition, comprising the step of incubating a T cell containing cell population ex vivo with a therapeutically effective amount of an isolated polypeptide comprising an NTB-A ectodomain or an agonist thereof.

2. The method of clause 1, wherein the incubation with the polypeptide or agonist is performed so as to up-regulate CD137 expression on T cells.
3. The method of clauses 1-2, wherein the population comprises CD8+ T cells.
4. The method of clauses 1-3 wherein the incubation is performed in the presence of T cell receptor (TCR) stimulation.
5. The method of clauses 1-4 wherein the incubation is performed in the presence of feeder cells.
6. The method of clauses 1-5 wherein the incubation is performed without the addition of exogenous IL-2.
7. The method of clauses 1-6 wherein the incubation is performed in the presence of exogenous CD137 ligand or an agonist thereof.
8. The method of clauses 1-7, wherein the composition is a cell vaccine.
9. The method of clauses 8, wherein the composition is a T cell vaccine.
10. A cell composition prepared by the method of any one of clauses 1-9
11. Use of a cell composition according to clause 10 for the preparation of a medicament for treating cancer in a subject in need thereof.
12. The use of clause 11, wherein the cell composition is histocompatible with said subject.
13. Use of a therapeutically effective amount of an isolated polypeptide comprising an NTB-A ectodomain or an agonist thereof for the preparation of a medicament for treating cancer in a subject in need thereof.
14. The use of any one of the preceding clauses, wherein the polypeptide comprises human NTB-A ectodomain.
15. The use of any one of the preceding clauses wherein the agonist is an antibody specific to an NTB-A ectodomain.
16. The use of clause 15 wherein the agonist is an antibody specific to human NTB-A ectodomain.
17. The use of any one of clauses 11-13, wherein said subject is afflicted with a tumor characterized by lack of substantial NTB-A surface expression.
18. The use of clause 17, wherein said tumor is a solid tumor.
19. The use of any one of clauses 11-13, wherein said subject is afflicted with a tumor characterized by surface expression of CD137.
20. The use of any one of clauses 11-13, wherein said subject is a cytopenic subject, or a subject at risk of developing cytopenia.
21. The use of any one of clauses 11-13, wherein said subject is afflicted with or at risk of developing lymphocytopenia.
22. The use of any one of clauses 11-13, wherein said subject is not afflicted with an active infectious disease, or with an acute or pathological inflammation.
23. The use of any one of clauses 11-13, wherein said subject is not afflicted with X-linked lymphoproliferative disease (XLP).
24. The use of any one of clauses 11-13, wherein exogenous IL-2 is not administered to said subject.
25. The use of any one of clauses 11-13, further comprising administering to said subject a CD137 ligand or an agonist thereof.
26. Use of a therapeutically effective amount of an isolated polypeptide comprising an NTB-A ectodomain or an agonist thereof for the preparation of a medicament for reducing or inhibiting T cell death.
27. The use of clause 26 wherein the contacting is performed in vitro.
28. The use of clause 26 wherein the contacting is performed in vivo.
29. The use of clause 26 for reducing or inhibiting T cell death in a subject suffering from or at risk of developing cytopenia.
30. Use of a therapeutically effective amount of a polypeptide comprising an NTB-A ectodomain or an agonist thereof for the preparation of a medicament for treating or preventing cytopenia in a subject in need thereof comprising administering to the subject.
31. The use of clause 30 wherein the cytopenia is associated with radiation or chemotherapy.
32. The use of clause 30 for the treatment or prevention of lymphocytopenia.
33. The use of clause 30 wherein said subject is not afflicted with an active infectious disease, or with an acute or pathological inflammation.
34. The use of clause 30 wherein said subject is not afflicted with X-linked lymphoproliferative disease (XLP).
35. The use of clause 30 wherein said subject is not afflicted with cancer.
36. The use of any one of clauses 26-35, wherein the polypeptide comprises human NTB-A ectodomain.
37. The use of any one of clauses 26-35 wherein the agonist is an antibody specific to human NTB-A ectodomain.
38. A therapeutic combination comprising 1) a polypeptide comprising an NTB-A ectodomain or an agonist thereof, 2) a polypeptide comprising CD137 ligand or an agonist thereof and optionally 3) a pharmaceutically acceptable carrier.
39. The combination of clause 38, comprising human NTB-A ectodomain.
40. The combination of clause 38, comprising human CD137 ligand.
41. The combination of clause 38, wherein the agonist is an antibody.

The following examples are presented in order to more fully illustrate some embodiments of the invention. They should, in no way be construed, however, as limiting the broad scope of the invention.

EXAMPLES

Example 1. Human NTB-A Ectodomain

A human NTB-A having an amino acid sequence as set forth below, corresponds to accession no. Q96DU3, as follows;

```
                                           (SEQ ID NO: 1)
MLWLFQSLLF VFCFGPGNVV SQSSLTPLMV NGILGESVTL

PLEFPAGEKV NFITWLFNET SLAFIVPHET KSPEIHVTNP

KQGKRLNFTQ SYSLQLSNLK MEDTGSYRAQ ISTKTSAKLS

SYTLRILRQL RNIQVTNHSQ LFQNMTCELH LTCSVEDADD

NVSFRWEALG NTLSSQPNLT VSWDPRISSE QDYTCIAENA

VSNLSFSVSA QKLCEDVKIQ YTDTKMILFM VSGICIVFGF

IILLLLVLRK RRDSLSLSTQ RTQGPAESAR NLEYVSVSPT

NNTVYASVTH SNRETEIWTP RENDTITIYS TINHSKESKP

TFSRATALDN VV
```

The ectodomain of this protein has been identified to be located at positions 22-226. Thus, an NTB-A ectodomain may have an amino acid sequence corresponding to positions 22-226 in the above human sequence, or to the corresponding positions in an NTB-A sequences known in the art. In other embodiments, the use of variants, homologs and derivatives thereof, which are recognized by a skilled artisan as structural and functional equivalents thereof, is contemplated (for example conservative amino acid substitutions). In addition, extensions and/or truncations of amino acids at either termini (e.g. 1-5 amino acids or up to 5%) may be permitted. According to certain advantageous embodiments, amino acids 1-21 are excluded. According to certain other advantageous embodiments, amino acids 1-27 are excluded.

For example, without limitation, an NTB-A ectodomain may comprise positions 22-226 of SEQ ID NO: 1. In other embodiments, the NTB-A ectodomain may consist essentially of positions 22-226 of SEQ ID NO: 1. In other embodiments, the NTB-A ectodomain may consist of positions 22-226 of SEQ ID NO: 1. In another embodiment, the NTB-A ectodomain may comprise positions 22-225 of SEQ ID NO: 1. In other embodiments, the NTB-A ectodomain may consist essentially of positions 22-225 of SEQ ID NO: 1. In other embodiments, the NTB-A ectodomain may consist of positions 22-225 of SEQ ID NO: 1. In another embodiment, the NTB-A ectodomain may comprise positions 28-225 of SEQ ID NO: 1. In other embodiments, the NTB-A ectodomain may consist essentially of positions 28-225 of SEQ ID NO: 1. In other embodiments, the NTB-A ectodomain may consist of positions 28-225 of SEQ ID NO: 1. In another embodiment, the NTB-A ectodomain may comprise positions 28-226 of SEQ ID NO: 1. In other embodiments, the NTB-A ectodomain may consist essentially of positions 28-226 of SEQ ID NO: 1. In other embodiments, the NTB-A ectodomain may consist of positions 28-226 of SEQ ID NO: 1. According to certain particular embodiments, said NTB-A ectodomain further comprises an epitope tag such as a polyhistidine tag. Each possibility represents a separate embodiment of the invention.

In the experiments described in the Examples below, recombinant human NTB-A was used, purchased from Novoprotein (cat. No. C387). The sequence of this protein corresponds in some embodiments to the extracellular domain of human NTB-A (positions Gln 22-Met 226 of accession no. Q96DU3, as set forth in SEQ ID NO: 2), fused with a polyhistidine tag at the C terminus. Unless otherwise indicated, throughout the Examples and Figures, "seSLAMF6" and "sNTB-A" refer to this recombinant fusion protein.

The sequence used in certain other Examples as indicated below corresponds to positions Leu 28-Lys 225 of accession no. Q96DU3 fused with a polyhistidine tag at the C-terminus (SEQ ID NO: 3, as follows:

```
LMVNGILGES VTLPLEFPAG EKVNFITWLF NETSLAFIVP

HETKSPEIHV TNPKQGKRLN FTQSYSLQLS NLKMEDTGSY

RAQISTKTSA KLSSYTLRIL RQLRNIQVTN HSQLFQNMTC

ELHLTCSVED ADDNVSFRWE ALGNTLSSQP NLTVSWDPRI

SSEQDYTCIA ENAVSNLSFS VSAQKLCEDV KIQYTDTKVD

HHHHHH).
```

Example 2. Specific Binding of seSLAMF6

Figure 1B:
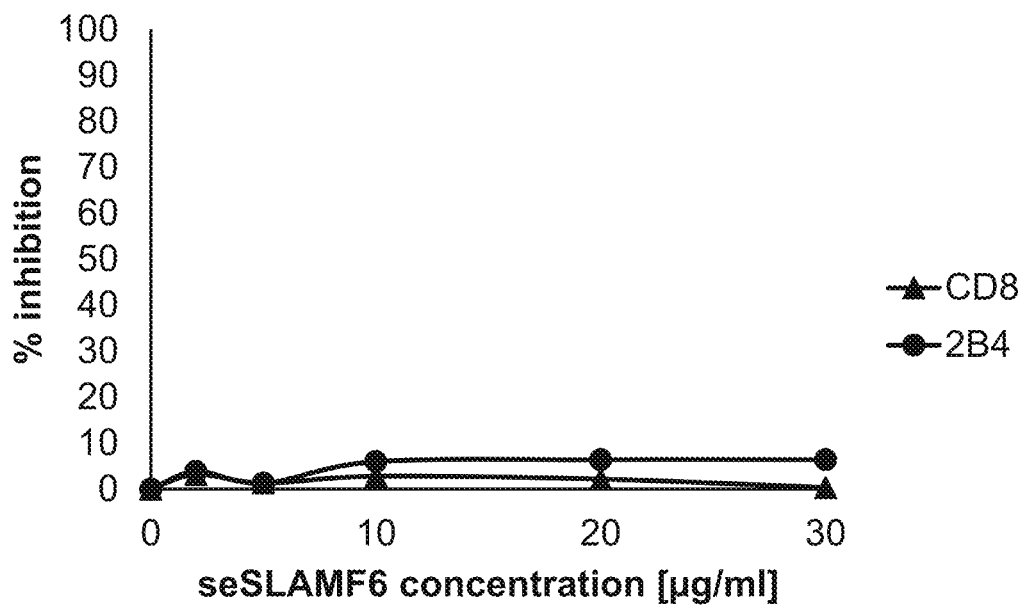

In order to demonstrate binding of seSLAMF6 to its homotypic receptor, human tumor infiltrating lymphocytes (TILs) were incubated with increasing concentrations of seSLAMF6 or with bovine serum albumin (BSA, irrelevant protein control). For these experiments, 200,000 TILs (209) in 100 μl FACS buffer were added to each FACS tube. Various sNTB-A(seSLAMF6) or BSA concentrations, ranging from 0 to 30 μg/ml were added to each tube and incubated at 4° C. for 45 min. Samples were washed once, and 10 μl PE-conjugated anti-seSLAMF6 antibody (clone NT-7, Biolegend) or isotype control were added to each tube (FIG. 1A). As an additional negative control, samples were also stained for CD8 and 2B4 receptors (FIG. 1B). After 45 min incubation at 4° C. the cells were washed and analyzed by flow cytometry. As can be seen in FIGS. 1A-B, seSLAMF6 completely inhibited binding of anti-SLAMF6 antibodies to tumor infiltrating lymphocytes (A), and did not inhibit binding of anti-CD8 and anti-2B4 antibodies to these surface receptors. The results from these experiments clearly demonstrate that the activity of seSLAMF6 is mediated by its binding to SLAMF6.

Figure 2A:
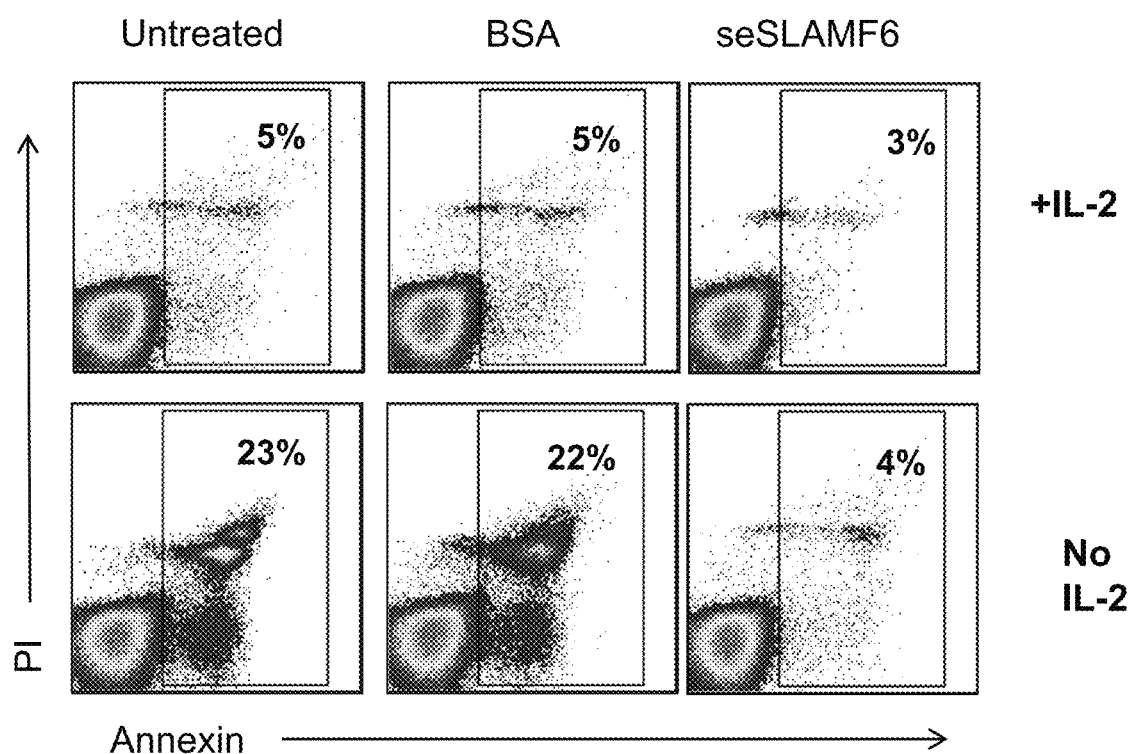
FIG. 2(A-C). SLAMF6 engagement by the soluble ectodomain (seSLAMF6) improves survival of activated human (FIG. 2A) and mouse (FIG. 2B) anti-melanoma T cells.
(FIG. 2C) SLAMF6 engagement by seSLAMF6 enhances post-REP survival in human TILs 7 days after the endpoint of the REP procedure.

Example 3. SLAMF6 Engagement by seSLAMF6 Improves Survival of Activated Anti-Melanoma T Cells Human TILs (209) were co-cultured with cognate melanoma cells (624mel) for 3 days (at a 1:4 ratio, in complete medium with IL-2 6,000 IU/ml, 37° C., 5% $CO_2$), and then allowed to proliferate in complete medium (CM) containing IL-2 (6000 IU/ml) for 7 days. After proliferation, IL-2 (6000 IU/ml) was further supplemented or withdrawn, and the cells were treated with either seSLAMF6 (SEQ ID NO: 3, 10 μg/ml) or BSA (10 μg/ml; ("control"), or remained untreated. Cells were labeled with propidium-iodide (PI), a marker of cell death, and Annexin-V, a marker of apoptosis, and analyzed by flow cytometry. FIG. 2A shows that the addition of seSLAMF6 reduced the ratio of cell death and apoptosis from 23% to 4%. The effect of seSLAMF6 was identical to that of IL-2, showing that SLAMF6 engagement can replace IL-2 and prevent activation-induced cell death (AICD).

In a different experiment, human TILs (209), reactive against 624mel, were co-cultured with the tumor for 72 hours. During the next 7 days cultures were supplemented with IL-2, 6000 IU/ml (IL-2+). Then IL-2 was removed from cultures, cells were washed three times to remove any remaining IL-2 and grown with or without seSLAMF6 (SEQ ID NO: 2 with a polyhistidine tag), and compared with an irrelevant protein control. In other words, seSLAMF6 was present in the cell cultures only during stress, when cells were IL-2-deprived for 4 days. Apoptosis and cell death were evaluated by flow cytometry. The results are summarized in Table 1 below (values represent % of Annexin$^+$ PI$^+$ cells from the total population). The results have shown that the addition of seSLAMF6 ectodomain completely compensated for the absence of IL-2. This experiment was repeated, with very similar results, 3 times for TIL 209 and once for TIL 431 (TILs from 2 human donors).

TABLE 1 seSLAMF6 restores T cell viability following IL-2 deprivation. Flow cytometry analysis of melanoma-activated TILs supplemented by IL-2 (IL-2+) or deprived of the cytokine (values represent % of Annexin$^+$ PI$^+$ cells from the total population).

|  | Untreated | BSA | seSLAMF6 |
| --- | --- | --- | --- |
| IL-2$^+$ | 11% | 15% | 14% |
| IL-2 deprivation | 34% | 42% | 9% |

Figure 2B:
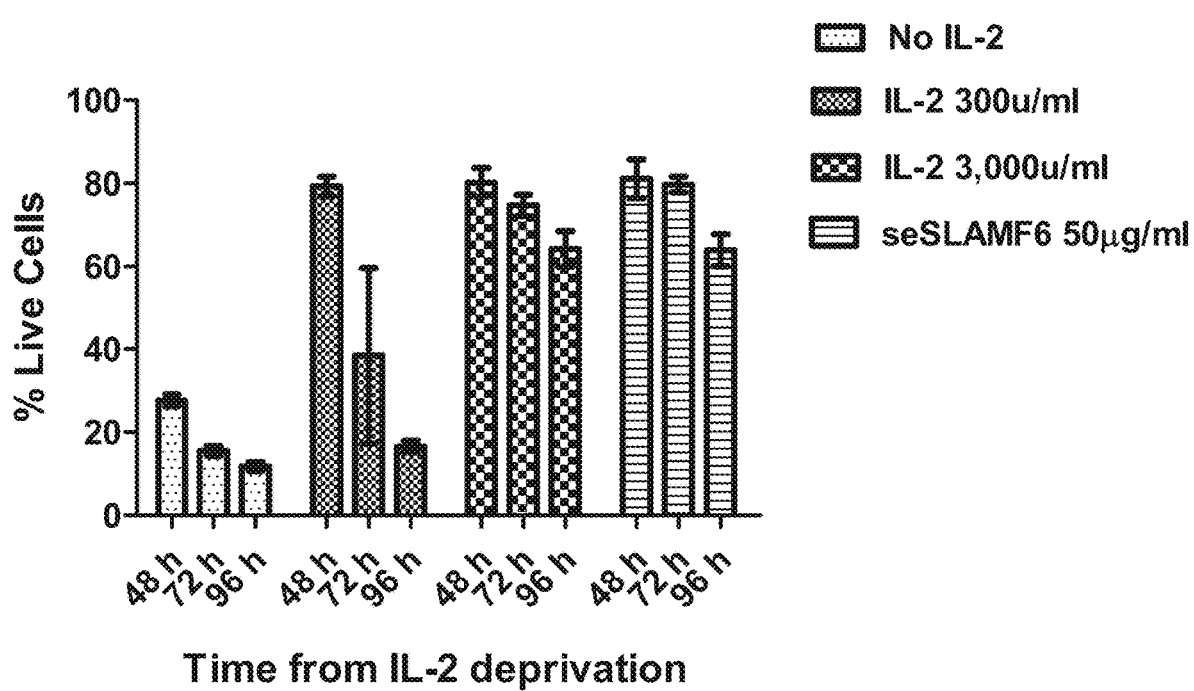

In a separate experiment Pmel-1 mouse splenocytes (expressing transgenic TCR against melanoma-antigen gp100$_{25-33}$) were stimulated with 1 g/ml cognate peptide (gp100$_{25-33}$) in CM supplemented with IL-2 (300 IU/ml). After 5 days, the cells were washed, and incubated for up to 96 hours in CM with 0, 300, 3000 IU/ml of IL-2 or with seSLAMF6 (SEQ ID NO: 3) (50 pg/ml). Cells were harvested at different time points and labeled with propidium-iodide (PI) and annexin-V. Death was determined by flow cytometry and the ratio of live cells was measured (percent of PI/Annexin-V negative cells from the entire population). The results are shown in FIG. 2B. As can be seen in the figure, seSLAMF6 was as efficient as the highest concentration of IL-2 (3000 IU/ml) in preventing AICD.

REP is a routine procedure to achieve the required number of tumor cognate lymphocytes for immunotherapy by adoptive cell transfer. Throughout the examples, where "REP" or "rapid expansion" is mentioned, this is to denote the presence of an incubation step for 12-14 days in the presence of inter alia 30 ng/ml of the OKT3 antibody and irradiated PBMC as feeder cells, at a ratio of TIL to PBMCs of 1:200 to 1:100.

Figure 2C:
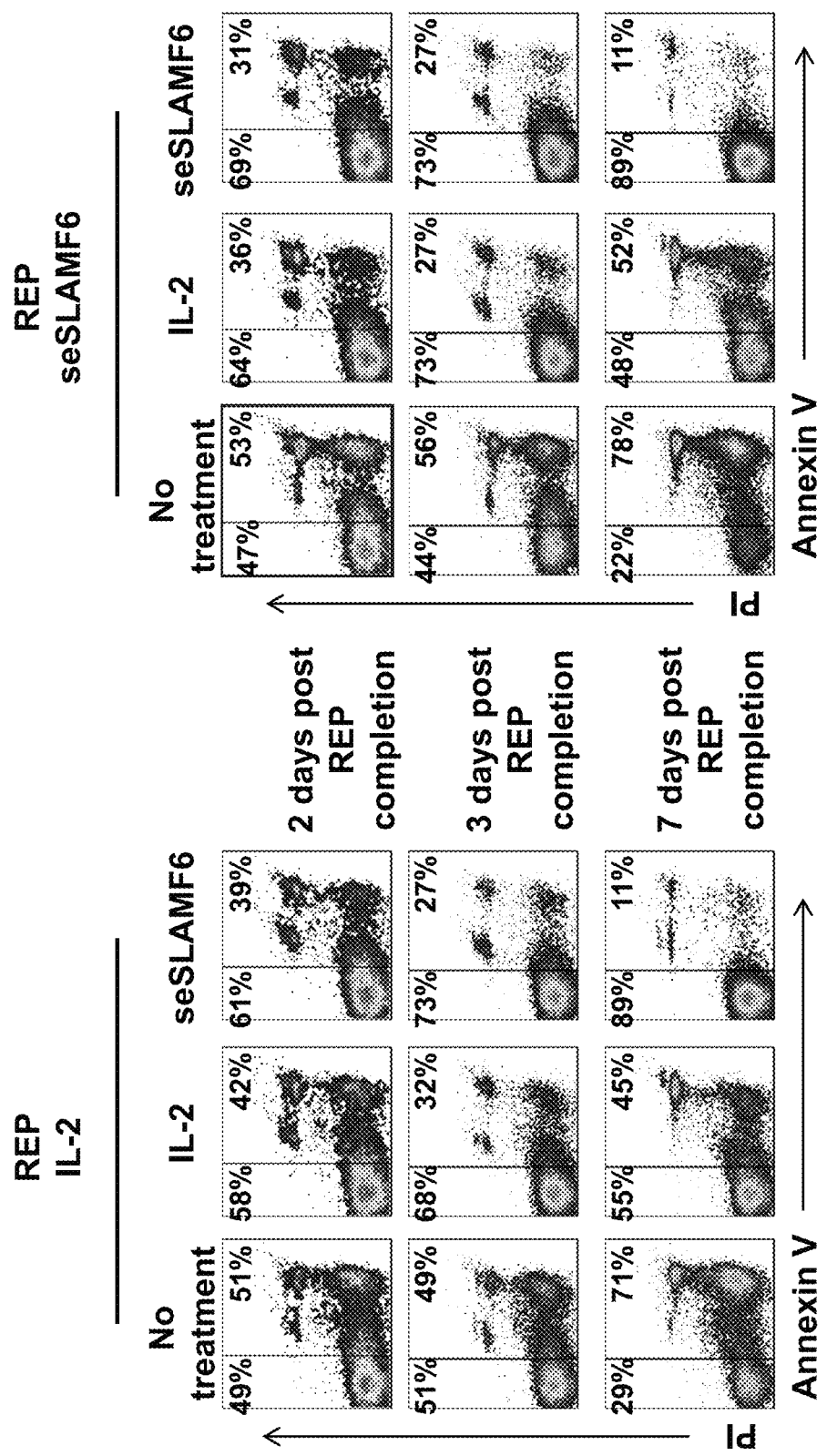

In a further experiment a human bulk TIL population (209) was expanded by REP using either CM supplemented with IL-2 (3,000 IU/ml) or seSLAMF6 (SEQ ID NO: 3) (50 pig/ml). At the end of the REP, cells were washed, and incubated under the following conditions: without IL-2 (no treatment), with IL-2 (300 IU/ml), or with seSLAMF6 (50 pig/ml). Cells were harvested at 2, 3 and 7 days, labeled with propidium-iodide (PI) and annexin-V, and cell death was measured by flow cytometry. The results are shown in FIG. 2C. As can be seen in the figure, the addition of seSLAMF6 to cells expanded by REP-IL-2 (left panel) reduced the ratio of cell death on Day 7 to 11%, compared to 71% in CM and 45% in IL-2. Similarly, the addition of seSLAMF6 to cells expanded by REP-seSLAMF6 (right panel) reduced the ratio of cell death on Day 7 to 11%, compared to 78% in CM and 52% in IL-2.

Example 4. SLAMF6 Engagement by seSLAMF6 Improves Function of Activated Anti-Melanoma T Cells IFNγ Production:

Pmel-1 mouse splenocytes were activated with 1 μg/ml cognate peptide (gp100$_{25-33}$) in CM supplemented with IL-2 (30 IU/ml). After 5 days, the cells were divided into three groups, each co-cultured for 6 hours with one of the following cell targets: 1. EL4-OVA, which are antigen-presenting cells stably transfected with ovalbumin (negative control); 2. B16-H2Db melanoma (gp100$_{25-33}$-containing melanoma cells with enhanced MHC class I expression); or 3. EL4 loaded with gp100, which are antigen-presenting cells pulsed with gp100$_{25-33}$ peptide (positive control). Each group was further divided into three sub-groups: treatment with seSLAMF6 (sNTBA, SEQ ID NO: 3, 50 μg/ml), treatment with BSA (50 μg/ml), and untreated cells.

Figure 3A:
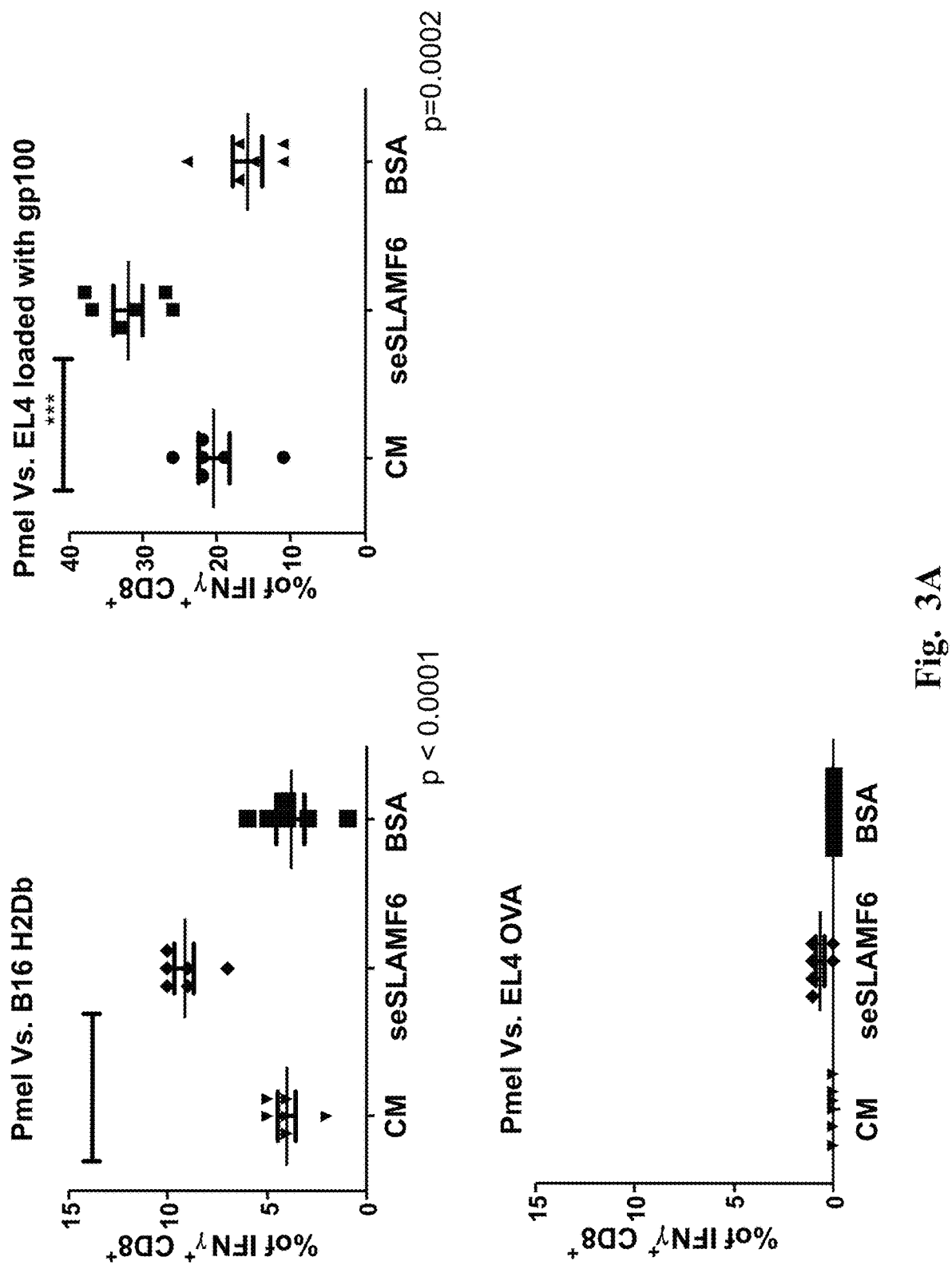
(FIG. 3A) SLAMF6 engagement by seSLAMF6 improves IFNγ production by mouse splenocyte.

Following the 6-hours co-culture the cells in each group were harvested, labeled with anti CD8/anti IFNγ intracellular staining, and subjected to flow cytometry acquisition and analysis. The results are shown in FIG. 3A (the data presented is a summary of 3 independent experiments). As can be seen in the figure, seSLAMF6 (SEQ ID NO: 3) enhanced the specific production of IFNγ by T cell clones: the addition of seSLAMF6 to the co-culture of the activated Pmel-1 mouse splenocytes with target cells (cognate melanoma or peptide-pulsed APCs) led to a significant increase in the percentage of cells producing IFNγ ($p<0.0001$ and $p<0.0002$, respectively).

In a different experiment, incubation of TIL with their cognate tumor cell lines in the presence of seSLAMF6 (SEQ ID NO: 2 with a C' His tag) increased IFNγ production. The A2-negative, non-cognate 888mel served as negative control. The addition of seSLAMF6 to the co-culture increased IFNγ secretion by 27% to 133% above baseline. No background activation was detected in the absence of melanoma recognition.

IFNγ Production Following REP:

In a further experiment, IFNγ production by bulk TILs after a 12-day procedure of rapid expansion (REP) with seSLAMF6 (SEQ ID NO: 2 with an added polyhistidine tag) was evaluated. The standard procedure of IL-2 supplementation (6000 IU/ml) was compared to exclusive supply of the soluble ectodomain of SLAMF6, 50 μg/ml.

Following REP, the T cells were co-cultured overnight (o/n) with cognate melanoma lines (624mel and 526mel) and IFN-γ secretion was measured. The results are summarized in Table 2 below. The results have shown that CD8$^+$ T cells expanded with seSLAMF6 produced remarkably higher levels of IFNγ following o/n incubation with the two cognate melanomas (526mel and 624mel).

TABLE 2

Lymphocytes which underwent expansion procedure supplemented with seSLAMF6 were endowed with superior IFN-γ secretion (values represent pg/ml of IFNγ).

|  | 624mel | 526mel |
| --- | --- | --- |
| Untreated | ~500 | ~200 |
| IL-2 300 IU | ~600 | ~700 |
| IL-2 6000 IU | ~900 | ~900 |
| SeSLAMF6 | ~4800 | ~3300 |

CD107a Expression (Lytic Degranulation):

Human TILs (209) were divided into three groups, each rapidly expanded under one of the following conditions: complete medium without IL-2, with IL-2 3,000 IU/ml or with seSLAMF6 (SEQ ID NO: 3) 50 μg/ml. After expansion, cells were harvested and washed. Each group was then further divided into three sub-groups: two co-cultured for 1.5 hours with one of the following cognate melanoma cell targets: 526mel or 624mel, and one co-cultured with 888mel, an HLA mismatch, to asses background activity.

Figure 3B:
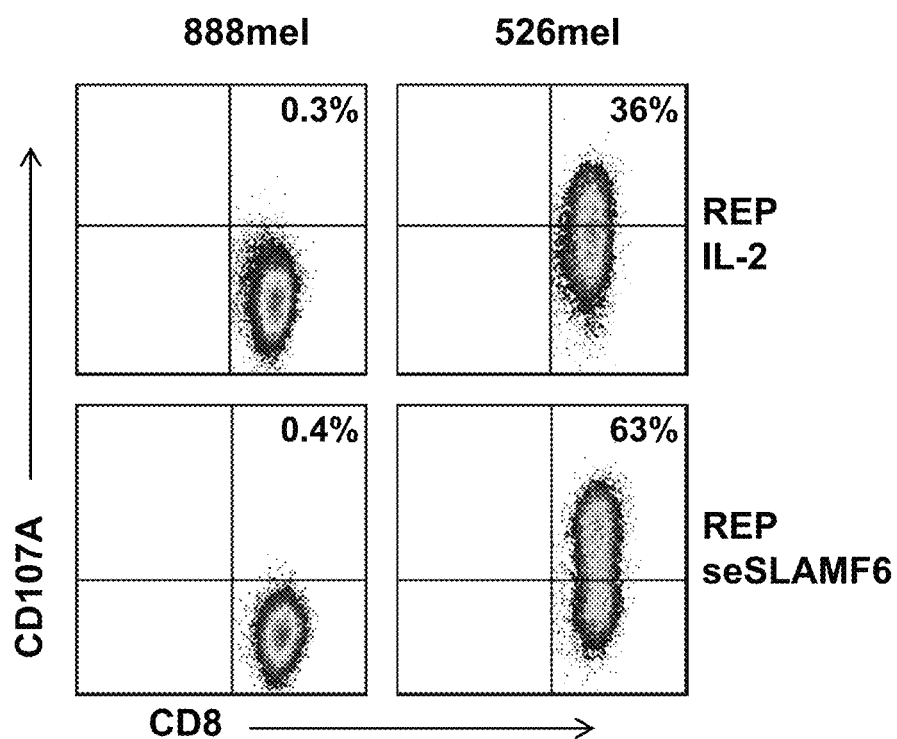
(FIG. 3B-3C) SLAMF6 engagement by seSLAMF6 during rapid expansion (B) and 3-day activation of human TIL (C) improves cytotoxicity assessed by CD107a mobilization.

After co-culture, cells were stained with anti-CD8 and anti-CD107a. CD107a (LAMP-1) is a lysosomal membrane protein. Its surface expression was evaluated here as a marker of lytic degranulation. The results are shown in FIG. 3B for 526mel cells. As can be seen in the figure, REP with seSLAMF6 yielded human TILs with about 2-fold increase in degranulation capacity. Similar results were obtained for 624mel cells.

Figure 3C:
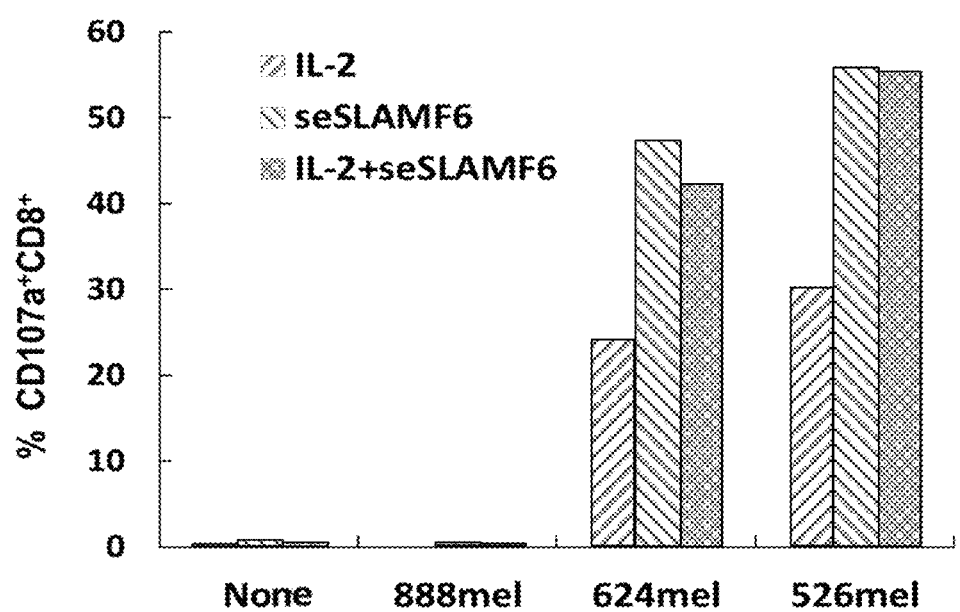

In a further experiment a human CD8+ T cell clone reactive against gp100$_{209-217}$ epitope was activated by plate-bound anti-CD3 for 3 days in complete medium supplemented with 300 U/ml IL-2, 50 μg/ml seSLAMF6 (SEQ ID NO: 3), or both. At the end of the activation period cells were co-cultured with HLA-A2-matched (624mel, 526mel) or irrelevant (888mel) melanoma targets for 1.5 hours. The level of CD107a, a marker for release of cytotoxic granules, was measured by flow cytometry. The results are shown in FIG. 3C. As can be seen in the figure, seSLAMF6 alone or in combination with IL-2 was superior to IL-2 alone in increasing degranulation capacity of the T cells.

Figure 3D:
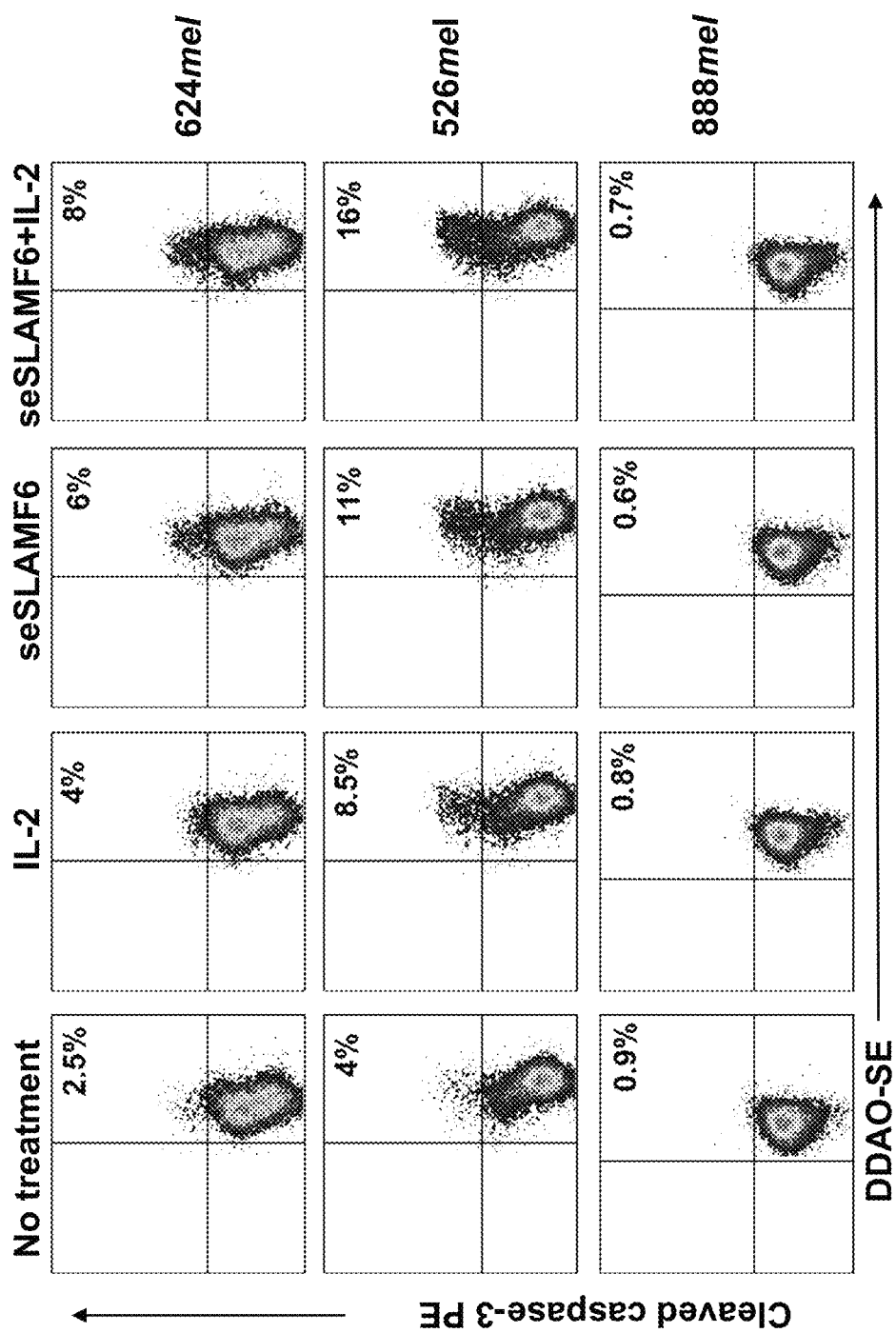
(FIG. 3D) SLAMF6 engagement by seSLAMF6 enhances melanoma cell killing by human CD8 T cells.

Cell Killing:

A human CD8+ T cell clone reactive against gp100$_{209-217}$ epitope was activated with plate-bound anti-CD3 for 5 days in CM with 1 µg/ml OKT3 alone (no treatment) or supplemented with 300 U/ml IL-2, 50 µg/ml seSLAMF6 (SEQ ID NO: 3) or both. At the end of the activation period cells were co-cultured with HLA-A2-matched (624mel, 526mel) or irrelevant (888mel) melanoma targets labeled with DDAO-SE for 1.5 hours. The level of intracellular cleaved caspase-3, an early marker for apoptosis, was measured in melanoma cells by flow cytometry. The results are shown in FIG. 3D. As can be seen in the figure, seSLAMF6 alone or in combination with IL-2 was superior to IL-2 alone in improving melanoma cell killing.

Figure 4:
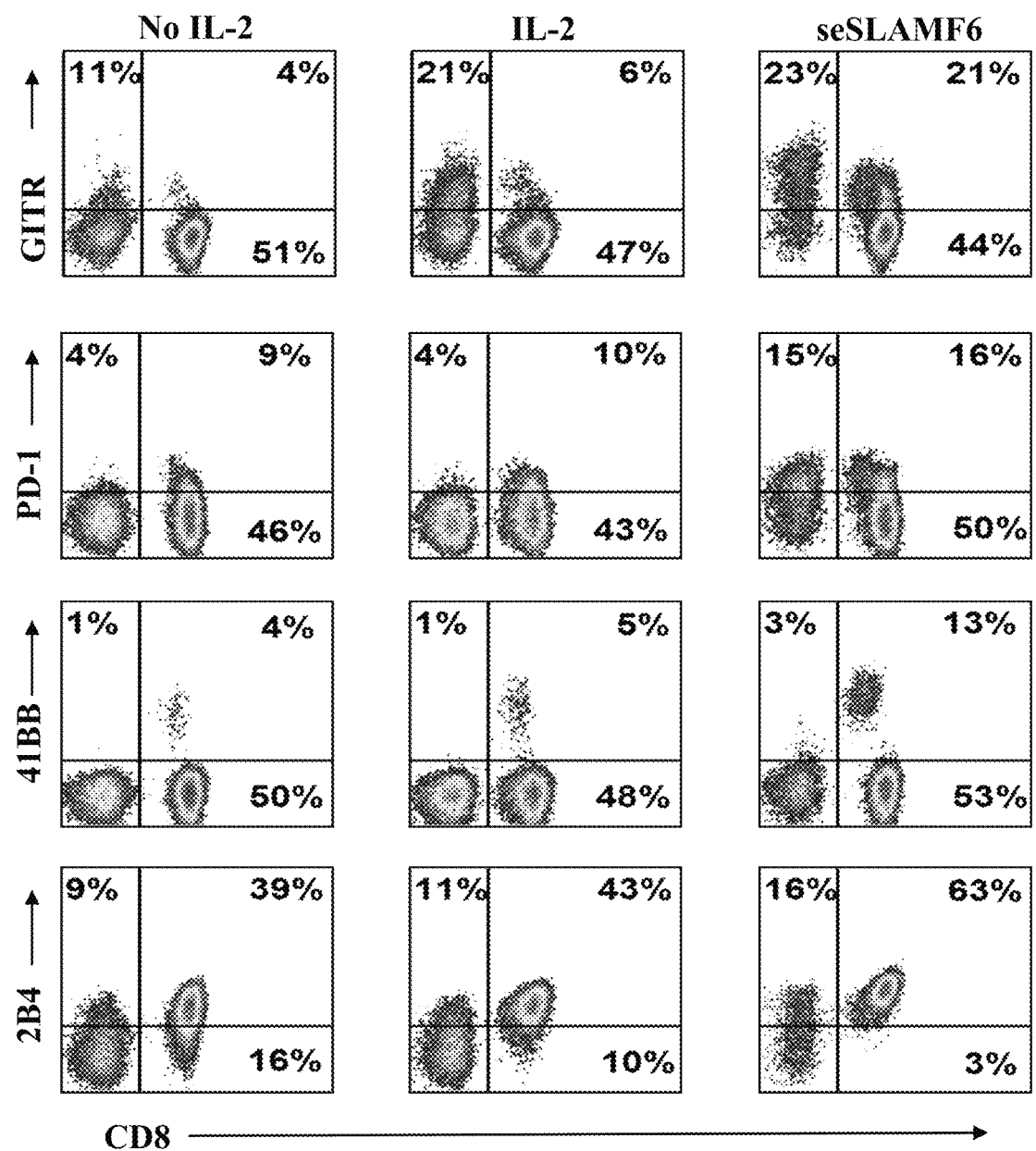
FIG. 4. SLAMF6 engagement by seSLAMF6 up-regulates expression of activation markers GITR, PD-1, 4-1BB (CD137) and SLAMF4 (2B4) on human TILs that underwent rapid expansion procedure (REP) supplemented by seSLAMF6.

Example 5. SLAMF6 Engagement by seSLAMF6 Up-Regulates Expression of Activation Markers Human TILs were rapidly expanded under the following conditions: complete medium without IL-2, IL-2 3,000 IU/ml or seSLAMF6 (SEQ ID NO: 3) 50 µg/ml. After expansion, cells were harvested, washed, and co-cultured overnight with melanoma targets 526mel and 624mel (cognate melanoma) and 888mel (HLA mismatch, to asses background activity). Following the overnight incubation, cells were harvested, stained with the following antibody panel: anti-CD8/anti-GITR/anti-PD-1/anti-41BB/anti-2B4, and analyzed by flow cytometry. The results are shown in FIG. 4 (the data presented is for cells co-cultured with the 526mel target). As can be seen in the figure, seSLAMF6 REP yielded the highest percent of lymphocytes expressing the tested activation-induced markers.

In a different experiment with the same setup as above, the effect of rapid expansion using seSLAMF6 (SEQ ID NO: 2 with an added polyhistidine tag) on the expression of the activation marker 4-1BB (CD137) was measured. The results are summarized in Table 3 below (values represent % of CD8$^+$4-1BB$^+$ cells from the total population). The results have shown that o/n incubation with two cognate melanomas (526mel and 624mel) doubled the number of 4-1BB-expressing cells in response to the tumor using seSLAMF6 for REP, compared to the standard use of IL-2.

TABLE 3

Rapid expansion procedure supplemented by seSLAMF6 doubled the percentage of lymphocytes capable of activation by cognate melanoma cells. Flow cytometry analysis of expanded lymphocytes (values represent % of CD8$^+$ 4-1BB$^+$ cells from the total population).

|  | Irrelevant melanoma | 526mel | 624mel |
|---|---|---|---|
| IL-2 | 1% | 9% | 8% |
| seSLAMF6 | 1% | 17% | 16% |

Example 6. SLAMF6 Engagement by seSLAMF6 can be Used to Expand TILs with the Same Efficiency of IL-2

Figure 5:
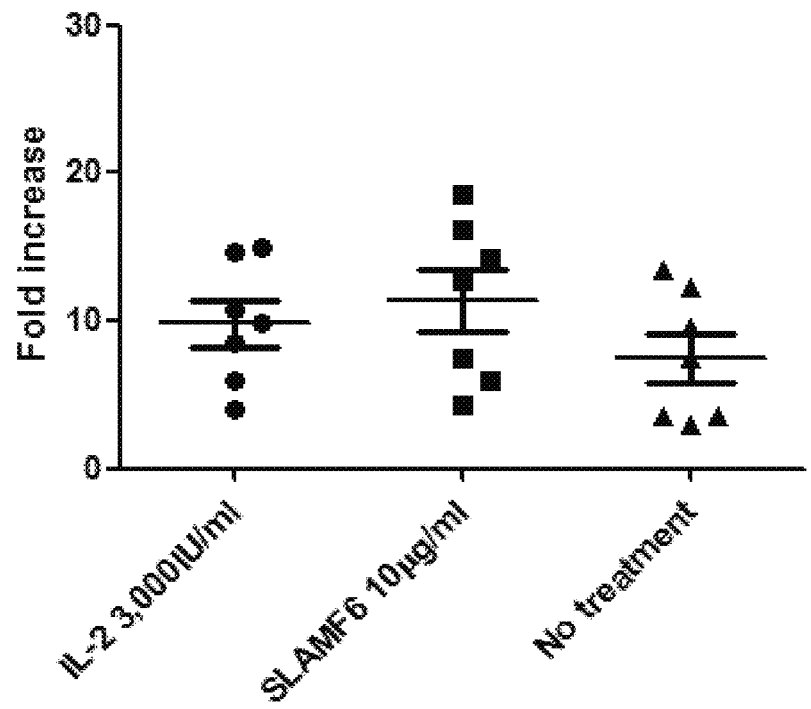
FIG. 5. SLAMF6 engagement by seSLAMF6 expands TILs with the same efficiency of IL-2.

Seven (7) different TIL populations (TIL 431 f(3), TIL 209 new, TIL 412 (11.09.12), Clone #4 (209) 13.4.14, Bulk 412, Clone #1 (209), Clone #4 (209) 10.6.14) were expanded by REP in complete medium using IL-2 (3,000 IU/ml) or seSLAMF6 (SEQ ID NO: 3, 10 µg/ml). Following expansion cells were counted and the final number of cells was compared to the initial cell number. The results are shown in FIG. 5 (presented as fold-increase in the number of cells). As can be seen in the figure, seSLAMF6 expanded the cells with substantially the same efficiency as IL-2.

Figure 6:
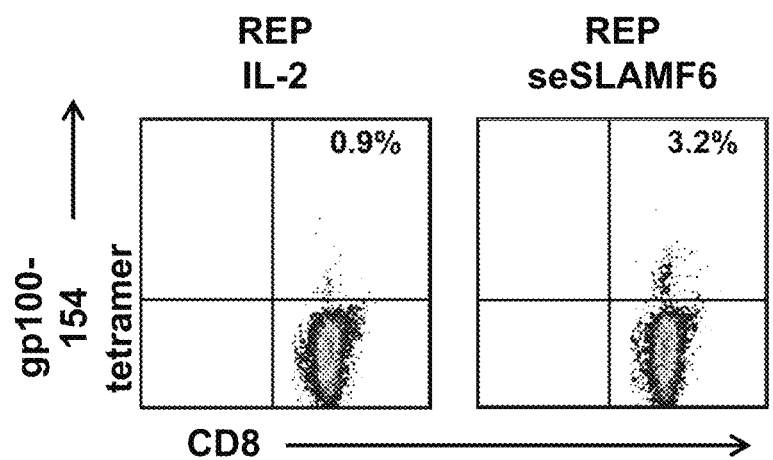
FIG. 6. SLAMF6 engagement by seSLAMF6 during REP yields a higher percent of melanoma-specific CD8 T cells.

Example 7. SLAMF6 Engagement by seSLAMF6 During REP Yields a Higher Percent of Melanoma-Specific CD8 T Cells The bulk TIL population described in Example 6 was further analyzed for the percentage of gp100154-162 reactive subset among total CD8+ lymphocytes. Following REP, cells were harvested, labeled with anti-CD8 and gp100154 tetramer (Immudex) and analyzed by flow cytometry. The results are shown in FIG. 6. As can be seen in the figure, seSLAMF6 yielded higher percentage of gp100154-162 reactive lymphocytes compared to IL-2.

Figure 7:
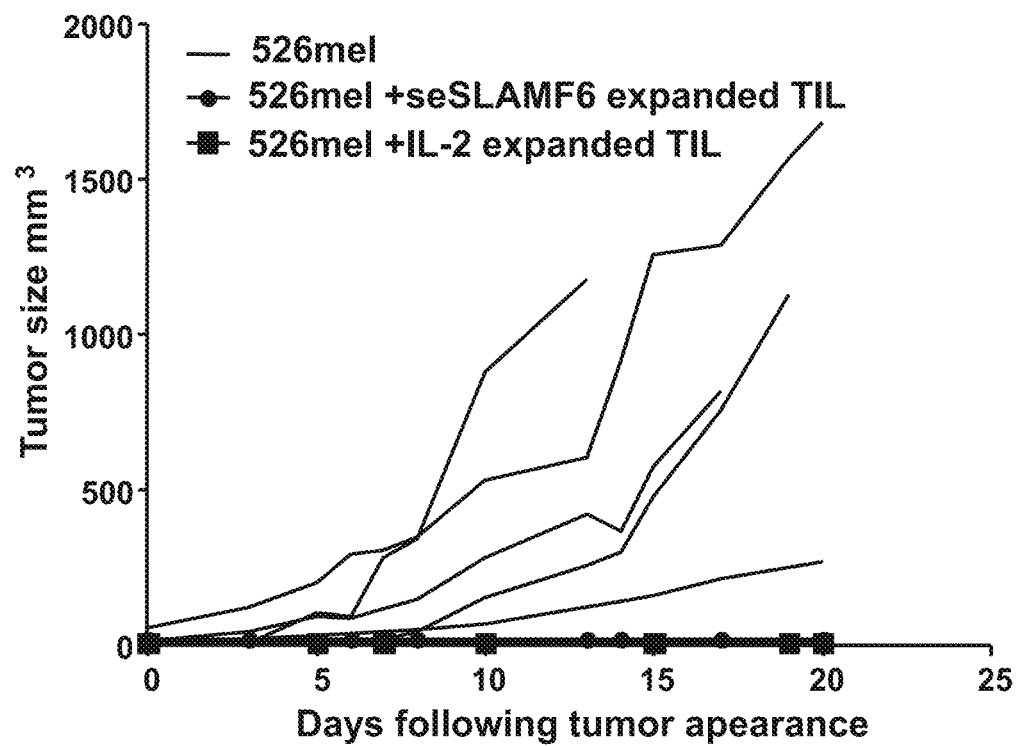
FIG. 7. Anti-melanoma TILs expanded with seSLAMF6 inhibit melanoma growth in vivo with the same efficiency as TILs expanded with the standard IL-2 protocol.

Example 8. Inhibition of Melanoma Growth by seSLAMF6-Expanded Anti-Melanoma TILs A human anti gp100$_{209-217}$ CD8$^+$ T cell clone was activated with plate-bound anti-CD3 for 5 days in CM supplemented with 300U/ml IL-2 or 50 µg/ml seSLAMF6. The activated cell population was used in a Winn assay: Athymic Foxn1$^{-/-}$ (nude) mice were injected subcutaneously (S.C) with 1×10$^6$ 526mel human melanoma cells. Prior to injection, the melanoma cells were mixed with CM (control), anti-gp100 human TILs grown with IL-2, or anti-gp100 human TILs grown with seSLAMF6. Tumor growth was monitored 3 times a week for 20 days. (n=5 per group). The results are shown in FIG. 7. As can be seen in the figure, seSLAMF6-expanded TILs completely inhibited melanoma growth during the follow-up period. Similar results were observed for IL-2-expanded TILs.

Example 9. seSLAMF6 Synergizes with 4-1BB (CD137) Ligation in the Production of IFN-γ by T Cell Clones In the experiments described below, melanoma 624mel transfected to express 4-1BBL or moc-transfected were co-cultured with MART-1$_{27-35}$-reactive T cell clones. As a control, the MART-1$_{27-35}$-reactive T cell clones were co-cultured with an irrelevant melanoma (mel888). The secretion of IFNγ from the T cells was measured, and the results are summarized in Table 4 below. Table 4 presents data demonstrating that this effect (IFNγ secretion) is markedly enhanced when the melanoma expresses 4-1BBL.

TABLE 4

IFNγ secretion of MART-1$_{27-35}$-reactive tumor infiltrating lymphocytes co-cultured with melanoma cells expressing 4-1BBL (mel624/4-1BBL), moc-transfected melanoma (mel624/moc) and irrelevant melanoma (mel888), following incubation in CM (complete medium), BSA (bovine serum albumin, used as control) and seSLAMF6 (values represent pg/ml of IFNγ).

| TIL 209(A2/MART1$_{27-25}$) | CM | BSA | seSLAMF6 |
|---|---|---|---|
| mel624/moc | 4,120 | 3,160 | 5,000 |
| mel624/4-1BBL | 8,600 | 10,540 | 12,000 |
| mel888 | 0 | 0 | 0 |

Example 10. SLAMF6 Engagement by the Soluble Ectodomain Increases Activation Markers on CD8+ T Cells Depending on TCR-Specific Recognition of Melanoma Cells Table 5 below demonstrates that the SLAMF6 ectodomain increases 4-1BB expression on activated CD8+ lymphocytes from three donors after overnight co-culture following 6, 16 and 24 hours of co-culture with two melanoma cell lines in a TCR-dependent manner.

TABLE 5 seSLAMF6 significantly increases the expression of 4-1BB on TILs: Flow cytometry analysis of 4-1BB (CD137) expression on TILs after incubation with melanoma lines (values represent % positive from total CD8+ cells).

| Melanoma line | TIL (A2+ MART-1 reactive) | CM (%) | HSA (%) | seSLAMF6 (%) |
|---|---|---|---|---|
| 526 (A2+) | 209 | 53 | 55 | <u>65</u> |
|  | 412 | 29 | 28 | 31 |
|  | 431 | 17 | 16 | <u>42</u> |
|  | 470(A2−) | 7 | 7 | <u>14</u> |
| 624 (A2+) | 209 | 69 | 66 | <u>78</u> |
|  | 412 | 30 | 37 | 41 |
|  | 431 | 20 | 29 | <u>61</u> |
|  | 470(A2−) | 11 | 9 | <u>15</u> |
| 888 (A2−) | 209 | 1.5 | 1 | <u>4</u> |
|  | 412 | 0.4 | 0.4 | 0.5 |
|  | 431 | 4 | 3 | <u>8</u> |

Two HLA-A2+ melanoma cell lines (526 and 624) and one control HLA-A2-(888) line were incubated with three A2+ MART-1-reactive TILs (209, 412, 431), or with a control TIL (470) in CM (complete medium), BSA (bovine serum albumin, used as control) and soluble ectodomain of SLAMF6. In most cases seSLAMF6 significantly increased the expression of 4-1BB on TILs (underlined values).

Example 11. The Soluble Ectodomain of SLAMF6 Protects Against Activation Induced Cell Death of CD8+ T Cells Following Irradiation The assay used to measure protection against activation induced cell death (T cell survival) was performed as follows. One million TILs were activated by co-culture with 250,000 624mel HLA-matched melanoma in 24 well plates with 2 ml culture media (CM) for 3 days. At this time point all melanoma cells died, therefore only TILs were left in the cultures. No IL-2 was added during the activation phase. TILs were expanded in the presence of 6000 units/ml IL-2 for 7-9 days. One ml medium was replaced by fresh CM every 1-2 days. Cells were transferred to 12 well and 6 well plates according to population expansion. Cells were washed three times with PBS to remove any remaining IL-2 and were exposed to shock: irradiation at various doses and analysis after 24h. Cells were then stained with PI and Annexin V and analyzed by flow cytometry. seSLAMF6 was added at different time points according to the three experimental stages (activation, expansion, shock) to assess its overall influence on T cell survival and to determine the relevant stage. ±IL-2 refers to IL-2 presence during the shock phase. To measure apoptosis, the Annexin V apoptosis detection kit (eBioscience #88-8007) was used according to the manufacturer's instructions. Briefly, cells were washed with PBS and with binding buffer. 5 µl Annexin V dye+100 µl binding buffer were added to each tube followed by 15 min incubation at room temperature in the dark. After additional washing, 5 µl PI dye+200 ul binding buffer were added to each tube, and the cells were analyzed by flow cytometry within 4 hours.

The Soluble Ectodomain of SLAMF6 Protects Against Irradiation Induced Death of PBMCs Cells In these experiments, 6-well culture plates were coated with 1 µg anti-CD3 (OKT3) and 1 µg anti-CD28 in 1 ml PBS per well at 4° C. overnight. PBS was removed and the wells were blocked with 2 ml CM for 1 hour at room temperature. $10^7$ PBMCs in 5 ml CM with 300 units IL-2/ml were added per well. Cells were allowed to undergo activation for 3 days, and then IL-2 was added every two days for additional 7 days. CM was replaced and cells were split as necessary. Cells were washed 3 times to remove remaining IL-2, and suspended in cold CM. Tubes were kept on ice, irradiated at escalating irradiation doses and washed immediately after irradiation with fresh CM. To the fresh medium 10 g/ml seSLAMF6 or BSA (control) were added. 24 hours later cells were stained with Annexin V & PI. PBMCs from two human donors were evaluated. Apoptosis and cell death were evaluated by flow cytometry. The results are summarized in Table 6 below (values represent % of Annexin+ PI+ cells from the total population). The results have shown that the addition of SLAMF6 ectodomain compensated for the damaging effects of irradiation at the same intensity as IL-2. SeSLAMF6 protects human PBMCs against damage caused by escalating doses of irradiation. The survival effect exerted by seSLAMF6 resembles the effect exerted by IL-2. This experiment was repeated with PBMCs from two human donors, with very similar results.

TABLE 6 seSLAMF6 restores T cell viability following irradiation. Values represent % of Annexin+ PI+ cells from the total population.

|  | 0 rad | 200 rad | 500 rad | 700 rad | 1000 rad |
|---|---|---|---|---|---|
| Untreated | 37% | 61% | 78% | 81% | 84% |
| IL-2 | 27% | 28% | 40% | 44% | 50% |
| seSLAMF6 | 26% | 36% | 49% | 53% | 59% |

REFERENCES

Krover et al., British Journal of Haematology 2007, 137, pp. 307-318.
Snow et al., Immunol Rev. 2010, 236, pp. 68-82.
Snow et al., J. Clin. Invest. 2009, 119, pp. 2976-2989.
Uzana et al., J Immunol 2012, 188, pp. 632-640.
Valdez et al, J Biol Chem 2004, 279(18), pp. 18662-18669.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed:

1. A method of treating cancer in a subject in need thereof, comprising administering to the subject a pharmaceutical composition comprising a therapeutically effective amount of an isolated NTB-A ectodomain, wherein said subject is afflicted with a tumor characterized by lack of NTB-A surface expression, wherein the isolated ectodomain lacks the signal peptide at positions 1-21 of NTB-A.

2. The method of claim 1, comprising administering to said subject an isolated NTB-A ectodomain consisting of the IgV and IgC2 domains and lacking the signal peptide of NTB-A.

3. The method of claim 1, wherein the NTB-A ectodomain is human NTB-A ectodomain.

4. The method of claim 1, wherein the NTB-A ectodomain further comprises an epitope tag and/or a serum half-life elongating substance.

5. The method of claim 1, wherein said subject is a cytopenic subject, or a subject at risk of developing cytopenia.

6. The method of claim 1, wherein IL-2 is not exogenously administered to said subject.

7. The method of claim 1, further comprising administering to said subject an extracellular portion of a CD137 ligand (CD137L) polypeptide, or an agonist antibody directed to CD137.

* * * * *

SEQUENCE LISTING

<160> NUMBER OF SEQ ID NOS: 5

<210> SEQ ID NO 1
<211> LENGTH: 332
<212> TYPE: PRT
<213> ORGANISM: Homo sapiens

<400> SEQUENCE: 1

Met Leu Trp Leu Phe Gln Ser Leu Leu Phe Val Phe Cys Phe Gly Pro
1               5                   10                  15

Gly Asn Val Val Ser Gln Ser Ser Leu Thr Pro Leu Met Val Asn Gly
            20                  25                  30

Ile Leu Gly Glu Ser Val Thr Leu Pro Leu Glu Phe Pro Ala Gly Glu
        35                  40                  45

Lys Val Asn Phe Ile Thr Trp Leu Phe Asn Glu Thr Ser Leu Ala Phe
50                  55                  60

Ile Val Pro His Glu Thr Lys Ser Pro Glu Ile His Val Thr Asn Pro
65                  70                  75                  80

Lys Gln Gly Lys Arg Leu Asn Phe Thr Gln Ser Tyr Ser Leu Gln Leu
                85                  90                  95

Ser Asn Leu Lys Met Glu Asp Thr Gly Ser Tyr Arg Ala Gln Ile Ser
            100                 105                 110

Thr Lys Thr Ser Ala Lys Leu Ser Ser Tyr Thr Leu Arg Ile Leu Arg
        115                 120                 125

Gln Leu Arg Asn Ile Gln Val Thr Asn His Ser Gln Leu Phe Gln Asn
130                 135                 140

Met Thr Cys Glu Leu His Leu Thr Cys Ser Val Glu Asp Ala Asp Asp
145                 150                 155                 160

Asn Val Ser Phe Arg Trp Glu Ala Leu Gly Asn Thr Leu Ser Ser Gln
                165                 170                 175

Pro Asn Leu Thr Val Ser Trp Asp Pro Arg Ile Ser Ser Glu Gln Asp
            180                 185                 190

Tyr Thr Cys Ile Ala Glu Asn Ala Val Ser Asn Leu Ser Phe Ser Val
        195                 200                 205

Ser Ala Gln Lys Leu Cys Glu Asp Val Lys Ile Gln Tyr Thr Asp Thr
210                 215                 220

Lys Met Ile Leu Phe Met Val Ser Gly Ile Cys Ile Val Phe Gly Phe
225                 230                 235                 240

Ile Ile Leu Leu Leu Leu Val Leu Arg Lys Arg Arg Asp Ser Leu Ser
                245                 250                 255

Leu Ser Thr Gln Arg Thr Gln Gly Pro Ala Glu Ser Ala Arg Asn Leu
            260                 265                 270

Glu Tyr Val Ser Val Ser Pro Thr Asn Asn Thr Val Tyr Ala Ser Val
        275                 280                 285

Thr His Ser Asn Arg Glu Thr Glu Ile Trp Thr Pro Arg Glu Asn Asp
290                 295                 300

Thr Ile Thr Ile Tyr Ser Thr Ile Asn His Ser Lys Glu Ser Lys Pro
305                 310                 315                 320

Thr Phe Ser Arg Ala Thr Ala Leu Asp Asn Val Val
                325                 330

<210> SEQ ID NO 2
<211> LENGTH: 205
<212> TYPE: PRT
<213> ORGANISM: Homo sapiens -continued

```
<400> SEQUENCE: 2

Gln Ser Ser Leu Thr Pro Leu Met Val Asn Gly Ile Leu Gly Glu Ser
1               5                   10                  15

Val Thr Leu Pro Leu Glu Phe Pro Ala Gly Glu Lys Val Asn Phe Ile
            20                  25                  30

Thr Trp Leu Phe Asn Glu Thr Ser Leu Ala Phe Ile Val Pro His Glu
        35                  40                  45

Thr Lys Ser Pro Glu Ile His Val Thr Asn Pro Lys Gln Gly Lys Arg
    50                  55                  60

Leu Asn Phe Thr Gln Ser Tyr Ser Leu Gln Leu Ser Asn Leu Lys Met
65                  70                  75                  80

Glu Asp Thr Gly Ser Tyr Arg Ala Gln Ile Ser Thr Lys Thr Ser Ala
                85                  90                  95

Lys Leu Ser Ser Tyr Thr Leu Arg Ile Leu Arg Gln Leu Arg Asn Ile
            100                 105                 110

Gln Val Thr Asn His Ser Gln Leu Phe Gln Asn Met Thr Cys Glu Leu
        115                 120                 125

His Leu Thr Cys Ser Val Glu Asp Ala Asp Asn Val Ser Phe Arg
    130                 135                 140

Trp Glu Ala Leu Gly Asn Thr Leu Ser Ser Gln Pro Asn Leu Thr Val
145                 150                 155                 160

Ser Trp Asp Pro Arg Ile Ser Ser Glu Gln Asp Tyr Thr Cys Ile Ala
                165                 170                 175

Glu Asn Ala Val Ser Asn Leu Ser Phe Ser Val Ser Ala Gln Lys Leu
            180                 185                 190

Cys Glu Asp Val Lys Ile Gln Tyr Thr Asp Thr Lys Met
        195                 200                 205

<210> SEQ ID NO 3
<211> LENGTH: 206
<212> TYPE: PRT
<213> ORGANISM: Artificial Sequence
<220> FEATURE:
<223> OTHER INFORMATION: fusion protein

<400> SEQUENCE: 3

Leu Met Val Asn Gly Ile Leu Gly Glu Ser Val Thr Leu Pro Leu Glu
1               5                   10                  15

Phe Pro Ala Gly Glu Lys Val Asn Phe Ile Thr Trp Leu Phe Asn Glu
            20                  25                  30

Thr Ser Leu Ala Phe Ile Val Pro His Glu Thr Lys Ser Pro Glu Ile
        35                  40                  45

His Val Thr Asn Pro Lys Gln Gly Lys Arg Leu Asn Phe Thr Gln Ser
    50                  55                  60

Tyr Ser Leu Gln Leu Ser Asn Leu Lys Met Glu Asp Thr Gly Ser Tyr
65                  70                  75                  80

Arg Ala Gln Ile Ser Thr Lys Thr Ser Ala Lys Leu Ser Ser Tyr Thr
                85                  90                  95

Leu Arg Ile Leu Arg Gln Leu Arg Asn Ile Gln Val Thr Asn His Ser
            100                 105                 110

Gln Leu Phe Gln Asn Met Thr Cys Glu Leu His Leu Thr Cys Ser Val
        115                 120                 125

Glu Asp Ala Asp Asn Val Ser Phe Arg Trp Glu Ala Leu Gly Asn
    130                 135                 140

Thr Leu Ser Ser Gln Pro Asn Leu Thr Val Ser Trp Asp Pro Arg Ile
```

```
                    145                 150                 155                 160

Ser Ser Glu Gln Asp Tyr Thr Cys Ile Ala Glu Asn Ala Val Ser Asn
                165                 170                 175

Leu Ser Phe Ser Val Ser Ala Gln Lys Leu Cys Glu Asp Val Lys Ile
                180                 185                 190

Gln Tyr Thr Asp Thr Lys Val Asp His His His His His His
                195                 200                 205
```

<210> SEQ ID NO 4
<211> LENGTH: 255
<212> TYPE: PRT
<213> ORGANISM: Homo sapiens

<400> SEQUENCE: 4

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
                35                  40                  45

Pro Pro Asn Ser Phe Ser Ala Gly Gly Gln Arg Thr Cys Asp Ile
            50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
                130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 5
<211> LENGTH: 185
<212> TYPE: PRT
<213> ORGANISM: Homo sapiens

<400> SEQUENCE: 5

```
Met Arg Glu Gly Pro Glu Leu Ser Pro Asp Asp Pro Ala Gly Leu Leu
1               5                   10                  15

Asp Leu Arg Gln Gly Met Phe Ala Gln Leu Val Ala Gln Asn Val Leu
```

-continued

```
                    20                  25                  30
Leu Ile Asp Gly Pro Leu Ser Trp Tyr Ser Asp Pro Gly Leu Ala Gly
            35                  40                  45

Val Ser Leu Thr Gly Gly Leu Ser Tyr Lys Glu Asp Thr Lys Glu Leu
            50                  55                  60

Val Val Ala Lys Ala Gly Val Tyr Tyr Val Phe Phe Gln Leu Glu Leu
65                  70                  75                  80

Arg Arg Val Val Ala Gly Glu Gly Ser Gly Ser Val Ser Leu Ala Leu
                85                  90                  95

His Leu Gln Pro Leu Arg Ser Ala Ala Gly Ala Ala Ala Leu Ala Leu
                100                 105                 110

Thr Val Asp Leu Pro Pro Ala Ser Ser Glu Ala Arg Asn Ser Ala Phe
            115                 120                 125

Gly Phe Gln Gly Arg Leu Leu His Leu Ser Ala Gly Gln Arg Leu Gly
        130                 135                 140

Val His Leu His Thr Glu Ala Arg Ala Arg His Ala Trp Gln Leu Thr
145                 150                 155                 160

Gln Gly Ala Thr Val Leu Gly Leu Phe Arg Val Thr Pro Glu Ile Pro
                165                 170                 175

Ala Gly Leu Pro Ser Pro Arg Ser Glu
                180                 185
```